(12) United States Patent
Heidenreich et al.

(10) Patent No.: US 7,361,752 B2
(45) Date of Patent: Apr. 22, 2008

(54) RNAI MODULATION OF MLL-AF4 AND USES THEREOF

(75) Inventors: Olaf Heidenreich, Tuebingen (DE); Hans-Peter Vornlocher, Bayreuth (DE); Philipp Hadwiger, Altenkunstadt (DE)

(73) Assignee: Alnylam Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 11/303,367

(22) Filed: Dec. 14, 2005

(65) Prior Publication Data

US 2006/0166918 A1    Jul. 27, 2006

Related U.S. Application Data

(60) Provisional application No. 60/698,414, filed on Jul. 12, 2005, provisional application No. 60/668,392, filed on Apr. 5, 2005, provisional application No. 60/635,936, filed on Dec. 14, 2004.

(51) Int. Cl.
C07H 21/04 (2006.01)
(52) U.S. Cl. .................................... 536/24.5
(58) Field of Classification Search ................ 536/24.5
See application file for complete search history.

(56) References Cited

U.S. PATENT DOCUMENTS

| | | | |
|---|---|---|---|
| 4,957,735 A | 9/1990 | Huang | |
| 5,013,556 A | 5/1991 | Woodle et al. | |
| 5,043,164 A | 8/1991 | Huang et al. | |
| 5,686,101 A | 11/1997 | Tagawa et al. | |
| 5,705,187 A | 1/1998 | Unger | |
| 5,817,856 A | 10/1998 | Tirosh et al. | |
| 5,820,873 A | 10/1998 | Choi et al. | |
| 5,853,755 A | 12/1998 | Foldvari | |
| 6,107,094 A | 8/2000 | Crooke | |
| 2003/0175950 A1* | 9/2003 | McSwiggen | ................ 435/325 |
| 2005/0107325 A1 | 5/2005 | Manoharan et al. | |
| 2005/0245475 A1 | 11/2005 | Khvorova et al. | |

FOREIGN PATENT DOCUMENTS

| | | |
|---|---|---|
| WO | WO 2004/064737 | 8/2004 |
| WO | WO 2004/080406 | 9/2004 |
| WO | WO 2004/094345 | 11/2004 |
| WO | WO 2004/094595 | 11/2004 |

OTHER PUBLICATIONS

T. Tuschl,□□Mammalian RNA interference: in RNAi, a guide to gene silencing, G. J. Hannon (ed.), Cold Spring Harbor Laboratory Press, Cold Spring Harbor, NY, 2003, 265-295.*
Allen et al., "Large unilamellar liposomes with low uptake into the reticuloendothelial system" *FEBS Lett.* 223:42-46 (1987).
Asou et al., "Establishment of a Human Acute Myeloid Leukemia Cell Line (Kasumi-1) With 8;21 Chromosome Translocation" *Blood* 77:2031-2036 (1991).
Ayton et al., "Molecular mechanisms of leukemogenesis mediated by MLL fusion proteins" *Oncogene* 20:5695-5707 (2001).
Banerjee et al., "Drug delivery system: targeting of pentamidines to specific sites using sugar grafted liposomes" *J. Antimicrob. Chemother.* 38:145-150 (1996).
Bursen et al., "Interaction of AF4 wild-type and AF4 • MLL fusion protein with SIAH proteins: indication for t(4;11) pathobiology?" *Oncogene* 23:6237-6249 (2004).
Byrom et al., "Inducing RNAi with siRNA Cocktails Generated by RNase III" *TechNotes* 10(1), Ambion [online], www.ambion.com/techlib/tn/101/4.html (2003).
Caslini et al., "Modulation of cell cycle by graded expression of MLL-AF4 fusion oncoprotein" *Leukemia* 18:1064-1071 (2004).
Cevc et al., "Ultraflexible vesicles, Transfersomes, have an extremely low pore penetration resistance and transport therapeutic amounts of insulin across the intact mammalian skin" *Biochim. Biophys. Acta* 1368:201-215 (1998).
Cheng et al., "RNA interference and human disease" *Mol. Genet. Metab.* 80:121-128 (2003).
Collins et al., "Continuous growth and differentiation of human myeloid leukaemic cells in suspension culture" *Nature* 270:347-349 (1977).
Domer et al., "Acute mixed-lineage leukemia t(4;11)(q21;a23) generates an *MLL-AF4* fusion product" *Proc. Natl. Acad. Sci. USA* 90:7884-7888 (1993).
Dörrie et al., "Regulation of CD95 expression and CD95-mediated cell death by interferon-γ in acute lymphoblastic leukemia with chromosomal translocation t(4;11)" *Leukemia* 13:1539-1547 (1999).
Downing et al., "The der(11)-Encoded MLL/AF-4 Fusion Transcript Is Consistently Detected in t(4;11)(q21;q23)-Containing Acute Lymphoblastic Leukemia" *Blood* 83:330-335 (1994).
Dunne et al., "The Apparent Uptake of Fluorescently Labeled siRNAs by Electroporated Cells Depends on the Fluorochrome" *Oligonucleotides* 13:375-380 (2003).
Dykxhoorn et al., "Killing the messenger: short RNAs that silence gene expression" *Nat. Rev. Mol. Cell Biol.* 4:457-467 (2003).
Elbashir et al., "Duplexes of 21-nucleotide RNAs mediate RNA interference in cultured mammalian cells" *Nature* 411:494-498 (2001).
Elbashir et al., "RNA interference is mediated by 21- and 22-nucleotide RNAs" *Genes Dev.* 15:188-200 (2001).
Ernst et al., "The role of *MLL* in hematopoiesis and leukemia" *Curr. Opin. Hematol.* 9:282-287 (2002).
Foldvari et al., "Clinical observations with topical liposome-encapsulated inteferon alpha for the treatment of genital papillomavirus infections" *J. Liposome Res.* 7:115-126 (1997).
Foldvari et al., "Liposome encapsulated prostaglandin $E_1$ in erectile dysfunction: correlation between in vitro delivery through foreskin and efficacy in patients" *Urology* 52:838-843 (1998).

(Continued)

*Primary Examiner*—Brian Whiteman
(74) *Attorney, Agent, or Firm*—Lowrie, Lando & Anastasi

(57) ABSTRACT

The invention relates to compositions and methods for modulating the expression of the MLL-AF4 fusion gene, and more particularly to the downregulation of MLL-AF4 by chemically modified oligonucleotides.

7 Claims, 5 Drawing Sheets

OTHER PUBLICATIONS

GenBank Accession No. D13979, "Homo sapiens mRNA for AML1-MTG8 fusion protein, complete cds" May 29, 2002.

GenBank Accession No. L11017, "Transponson Tn5Tac1 (from *E coli*) DNA sequence" Jun. 20, 2002.

GenBank Accession No. L22179, "Human MLL-AF4 der(11) fusion protein mRNA, complete cds" Sep. 15, 1993.

GenBank Accession No. M15077, "*P.pyralis* (firefly) luciferase gene, complete cds" Apr. 26, 1993.

Greil et al., "Suppression of MLL-AF4 by Small Interfering RNAs Inhibits Proliferation and Induces Apoptosis in T(4;11)-Positive SEM Cells" *Blood* 104:191b, Abstract No. 4433 (2004).

Greil et al., "The acute lymphoblastic leukaemia cell line SEM with t(4;11) chromosomal rearrangement is biphenotypic and responsive to interleukin-7" *Br. J. Haematol.* 86:275-283 (1994).

Gu et al., "The t(4;11) Chromosome Translocation of Human Acute Leukemias Fuses the *ALL-1* Gene, Related to *Drosophila trithorax*, to the *AF-4* Gene" *Cell* 71:701-708 (1992).

Heidenreich, "Oncogene Suppression by Small Interfering RNAs" *Curr. Pharm. Biotechnol.* 5:349-354 (2004).

Heidenreich et al., "AML1/MTG8 oncogene suppression by small interfering RNAs supports myeloid differentiation of t(8;21)-positive leukemic cells" *Blood* 101:3157-3163 (2003).

Ho et al., "Interactions of Target-sensitive Immunoliposomes with Herpes Simplex Virus" *J. Biol. Chem.* 262:13797-13984 (1987).

Ho et al., "Target-sensitive Immunoliposomes as an Efficient Drug Carrier for Antiviral Activity" *J. Biol. Chem.* 262:13973-13978 (1987).

Hsieh et al., "Proteolytic Cleavage of MLL Generates a Complex of N- and C-Terminal Fragments That Confers Protein Stability and Subnuclear Localization" *Mol. Cell. Biol.* 23:186-194 (2003).

Hsieh et al., "Taspase1: A Threonine Aspartase Required for Cleavage of MLL and Proper *HOX* Gene Expression" *Cell* 115:293-303 (2003).

Isnard et al., "Altered lymphoid development in mice deficient for the mAF4 proto-oncogene" *Blood* 96:705-710 (2000).

Kersey et al., "Resistance of t(4;11) (MLL-AF4 fusion gene) leukemias to stress-induced cell death: possible mechanism for the extensive extamedullary accumulation of cells and poor prognosis" *Leukemia* 12:1561-1564 (1998).

Khvorova et al., "Functional siRNAs and miRNAs Exhibit Strand Bias" *Cell* 115:209-216 (2003).

Klibanov et al., "Amphipathic polyethyleneglycols effectively prolong the circulation time of liposomes" *FEBS Lett.* 268:235-237 (1990).

Lange et al., "Biological Markers in Urologic Cancer" *Cancer* 60:464-472 (1987).

Li et al., "AF4 Encodes a Ubiquitous Protein That in Both Native and MLL-AF4 Fusion Types Localizes to Subnuclear Compartments" *Blood* 92:3841-3847 (1998).

Limbach et al., "Summary: the modified nuclesides of RNA" *Nucleic Acids Res.* 22:2183-2196 (1994).

Lozzio et al., "*Brief Communication*: Cytotoxicity of a Factor Isolated From Human Spleen" *J. Natl. Cancer Inst.* 50:535-538 (1973).

Marschalek et al., "Molecular analysis of the chromosomal breakpoint and fusion transcripts in the acute lymphoblastic SEM cell line with chromosomal translocation t(4;11)" *Br. J. Haematol.* 90:308-320 (1995).

Martinez et al., "The oncogenic fusion protein RUNX1-CBFA2T1 supports proliferation and inhibits senescence in t(8;21)-positive leukaemic cells" *BMC Cancer* 4:44 (2004).

Mastrobattista et al., "Cellular uptake of liposomes targeted to intercellular adhesion molecule-1 (ICAM-1) on bronchial epithelial cells" *Biochim. Biophys. Acta* 1419:353-363 (1999).

Mastrobattista et al., "Immunoliposomes for the targeted delivery of antitumor drugs" *Adv. Drug Deliv. Rev.* 40:103-127 (1999).

Matozaki et al., "Establishment of a myeloid leukaemic cell line (SKNO-1) from a patient with t(8;21) who acquired monosomy 17 during disease progression" *Br. J. Haematol.* 89:805-811 (1995).

McCabe et al., "Cloning of cDNAS of the *MLL* gene that detect DNA rearrangements and altered RNA transcripts in human leukemic cells with 11q23 translocations" *Proc. Natl. Acad. Sci. USA* 89:11794-11798 (1992).

Meister et al., "Human Argonaute2 Mediates RNA Cleavage Targeted by miRNAs and siRNAs" *Mol. Cell* 15:185-197 (2004).

Mukhopadhyay et al., "Circumvention of multidrug resistance in neoplastic cells through scavenger receptor mediated drug delivery" *FEBS Lett.* 376:95-98 (1995).

Nakamura et al., "ALL-1 Is a Histone Methyltransferase that Assembles a Supercomplex of Proteins Involved in Transcriptional Regulation" *Mol. Cell* 10:1119-1128 (2002).

Pocock et al., "BCL-2 expression by leukaemic blasts in a SCID mouse model of biphenotypic leukaemia associated with the t(4;11)(q21;q23) translocation" *Br. J. Haematol.* 90:855-867 (1995).

Pui et al., "Outcome of treatment in childhood acute lymphoblastic leukaemia with rearrangements of the 11q23 chromosomal region" *Lancet* 359:1909-1915 (2002).

Rabbitts, "Chromosomal translocations in human cancer" *Nature* 372:143-149 (1994).

Rand et al., "Biochemical identification fo Argonaute 2 as the sole protein required for RNA-induced silencing complex activity" *Proc. Natl. Acad. Sci. USA* 101:14385-14389 (2004).

Reichel et al., "Biased distributed of chromosomal breakpoints involving the *MLL* gene in infants versus children and adults with t(4;11) ALL" *Oncogene* 20:2900-2907 (2001).

Scherr et al., "Specific inhibition of *bcr-abl* gene expression by small interfering RNA" *Blood* 101:1566-1569 (2003).

Schwartz et al., "Asymmetry in the Assembly of the RNAi Enzyme Complex" *Cell* 115:199-208 (2003).

Sharma et al., "Nova Taxol® Formulation: Polyvinylpyrrolidone Nanoparticle-Encapsulated Taxol® for Drug Delivery and Cancer Therapy" *Oncol. Res.* 8:281-286 (1996).

Sharma et al., "Thermosensitive liposomal taxol formulation: heat-mediated targeted drug delivery in murine melanoma" *Melanoma Res.* 8:240-244 (1998).

Short et al., "Percutaneous Absorption of Biologically-Active Interferon-gamma in a Human Skin Graft-Nude Mouse Model" *Pharm. Res.* 13:1020-1027 (1996).

Sledz et al., "Activation of the interferon system by short-interfering RNAs" *Nat. Cell Biol.* 5:834-839 (2003).

Song et al., "Crystal Structure of Argonaute and Its Implications for RISC Slicer Activity" *Science* 305:1434-1437 (2004).

Stong et al., "Human Acute Leukemia Cell Line With the t(4;11) Chromosomal Rearrangement exhibits B Lineage and Monocytic Characteristics" *Blood* 65:21-31 (1985).

Sundström et al., "Establishment and characterization of a human histiocytic lymphoma cell ine (U-937)" *Int. J. Cancer* 17:565-577 (1976).

Templeton et al., "Improved DNA: liposome complexes for increased systemic delivery and gene expression" *Nat. Biotechnol.* 15:647-652 (1997).

Torchilin et al., "*p*-Nitrophenylcarbonyl-PEG-PE-liposomes: fast and simple attachment of specific ligands, including monoclonal antibodies, to distal ends of PEG chains via *p*-nitrophenylcarbonyl groups" *Biochim. Biophys. Acta* 1511:397-411 (2001).

Torchilin et al., "TAT peptide on the surface of liposomes affords their efficient intracellular delivery even at low temperature and in the presence of metabolic inhibitors" *Proc. Natl. Acad. Sci. USA* 98:8786-8791 (2001).

Uckun et al., "Leukemic Cell Growth in SCID Mice as a Predictor of Relapse in High-Risk B-Lineage Acute Lymphoblastic Leukemia" *Blood* 85:873-878 (1995).

Witschi et al., "In Vitro Evaluation of Microparticles and Polymer Gels for Use as Nasal Platforms for Protein Delivery" *Pharm. Res.* 16:382-390 (1999).

Woodle et al., "Sterically stabilized liposomes" *Biochim. Biophys. Acta* 1113:171-199 (1992).

Yang et al., "Short RNA duplexes produced by hydrolysis with *Escherichia coli* RNase III mediate effective RNA interference in mammalian cells" *Proc. Natl. Acad. Sci.* USA 99:9942-9947 (2002).

Yeh et al., "Improving Protein Delivery from Microparticles Using Blends of Poly(DL lactide co-glycolide) and Poly(ethylene oxide)-poly(propylene oxide) Copolymers" *Pharm. Res.* 13:1693-1698 (1996).

Yokoyama et al., "Leukemia proto-oncoprotein MLL is proteolytically processed into 2 fragments with opposite transcriptional properties" *Blood* 100:3710-3718 (2002).

Yu et al., "MLL, a mammalian *trithorax* -group gene, functions as a transcriptional maintenance factor in morphogenesis" *Proc. Natl. Acad. Sci.* USA 95:10632-10636 (1998).

Zelphati et al., "Intracellular Delivery of Proteins with a New Lipid-mediated Delivery System" *J. Biol. Chem.* 276:35103-35110 (2001).

* cited by examiner

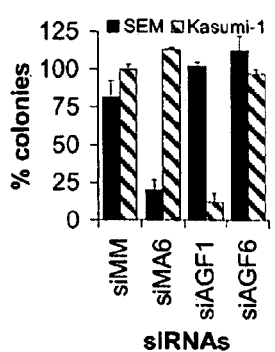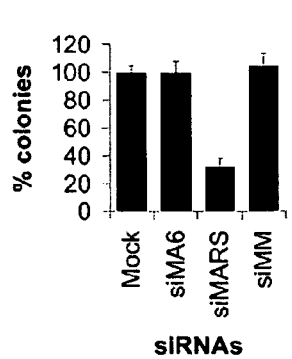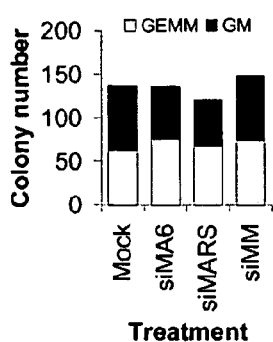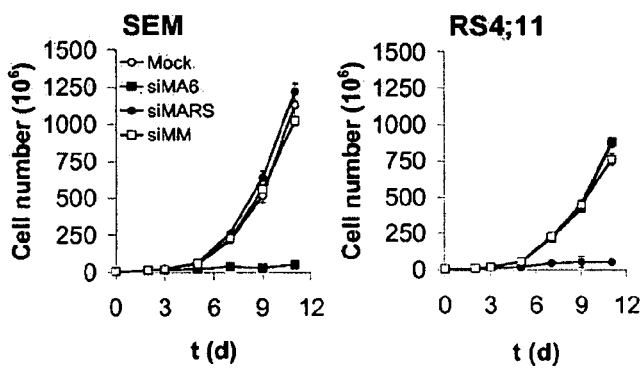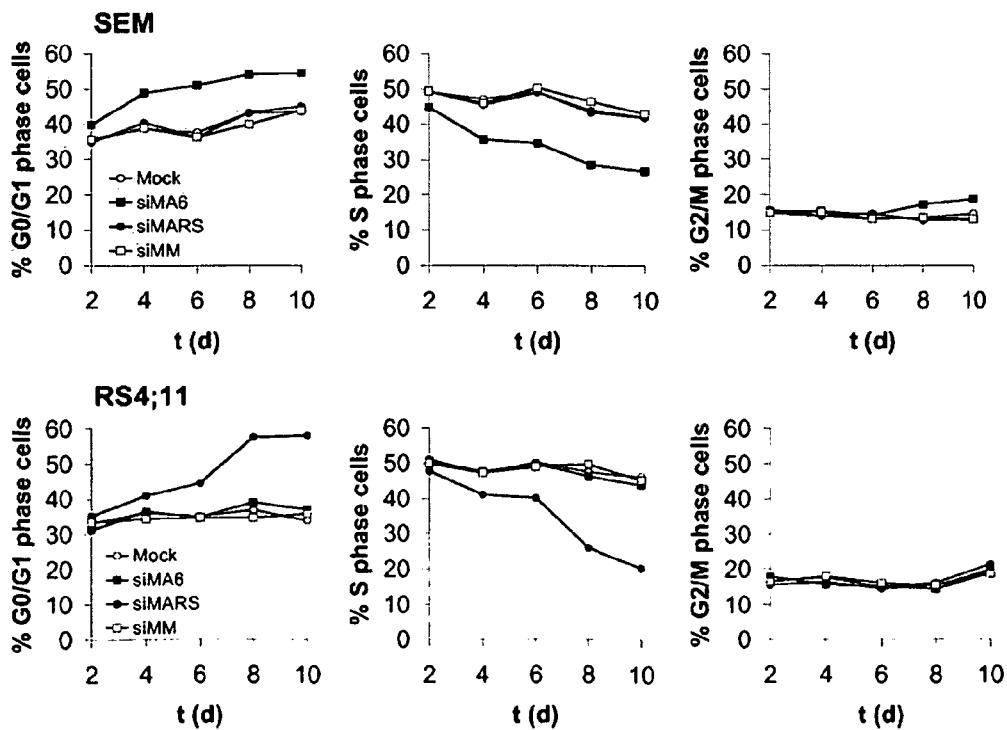

RNAI MODULATION OF MLL-AF4 AND USES THEREOF

RELATED APPLICATIONS

This application claims the benefit of U.S. Provisional Application No. 60/635,936, filed Dec. 14, 2004, U.S. Provisional Application No. 60/668,392, filed Apr. 5, 2005, and U.S. Provisional Application No. 60/698,414, filed Jul. 12, 2005. All three provisional applications are incorporated herein by reference in their entirety.

TECHNICAL FIELD

The invention relates to compositions and methods for modulating the expression of MLL-AF4, and more particularly to the downregulation of MLL-AF4 by chemically modified oligonucleotides.

BACKGROUND

Chromosomal aberrations giving rise to fusion genes are observed for many different leukemias (Rabbitts, T. H.; Nature 1994; 372: 143-149). Such tumor-specific oncogenes would be promising targets for new therapeutic approaches with increased specificity, if these oncogenes were important for maintaining the leukemic phenotype. However, in contrast to the development of a leukemia, a central role for its persistence has only been established for a minority of leukemic fusion genes.

The mixed lineage leukaemia (MLL) gene located on chromosome 11q23 is involved in numerous chromosomal translocations associated with human leukemia (Ernst, P., et al.; Curr Opin Hematol 2002; 9:282-287). The most prevalent among those is the translocation t(4;11)(q21;q23), which fuses MLL gene with the AF4 gene located on chromosome 4q21 (Gu, Y., et al.; Cell 1992; 71:701-708.; McCabe, N. R., et al.; Proc Natl Acad Sci USA 1992; 89:11794-11798; Domer, P. H., et al.; Proc Natl Acad Sci USA 1993; 90:7884-7888.). This translocation is the hallmark of a high-risk acute lymphoblastic leukemia (ALL) with a particularly poor prognosis in infants (Pui, C. H., et al.; Lancet 2002; 359:1909-1915).

The wild-type MLL gene is a member of the trithorax family and encodes for a 431 kD protein, which is proteolytically processed into two fragments —300 and 180 kD heterodimerizing with each other (Nakamura, T., et al.; Mol Cell 2002; 10:1119-1128; Yokoyama, A., et al.; Blood 2002; 100:3710-3718; Hsieh, J. J., et al.; Cell 2003; 115:293-303; Hsieh, J. J., et al.; Mol Cell Biol 2003; 23:186-194.). The MLL protein has a complex structure that includes an AT-hook domain for DNA-binding, a MT domain showing homology to DNA methyltransferase (DMT) and methyl binding domain protein 1 (MBD1), a plant homeodomain (PHD) containing zinc fingers and a SET histone methyl transferase domain (Ernst, P., et al.; Curr Opin Hematol 2002; 9:282-287). MLL is involved in mechanisms controlling hox genes transcription (Ayton, P. M., and Cleary, M. L.; Oncogene 2001; 20:5695-5707.). Interestingly, the Hox genes Hoxa7 and Hoxa9 in combination with the homeotic gene Meis-1 are necessary for the transfomation induced by several different MLL fusion genes. Such a crucial role has not yet been reported for MLL-AF4. Nevertheless, expression levels of all three homeotic genes are raised in primary t(4;11) ALL.

The AF4 gene encodes a serine/proline-rich protein containing nuclear localization signal and GTP-binding domain. It localizes to the nucleus (Li, Q., et al.; Blood 1998; 92:3841-3847) and is probably involved in transcriptional activation functions. Whereas the MLL knockout is embryonally lethal (Yu, B. D., et al.; Proc Natl Acad Sci USA 1998; 95:10632-10636), AF4-deficient mice exhibit imperfect T-cell development and modest alterations in B-cell development (Isnard, P., et al.; Blood 2000; 96:705-710).

Notably, the t(4;11) translocation generates two fusion genes, AF4-MLL and MLL-AF4. The significance of either fusion gene for leukemogenesis is not completely understood yet. AF4-MLL has recently been shown to interfere with ubiquitin-mediated AF4 degradation and to transform murine embryonic fibroblasts (Bursen, A., et al.; Oncogene 2004; 23:6237-6249). Ectopic expression of MLL-AF4 in t(4;11)-negative leukemic cell lines, however, inhibits cell cycle progression and triggers apoptosis (Caslini, C., et al.; Leukemia 2004; 18:1064-1071). Paradoxically, 20% of all (4;11) ALL patients lack AF4-MLL either on the transcriptional or genomic level, whereas MLL-AF4 is always detectable despite its proapoptotic activities upon ectopic expression (Downing, J. R., et al.; Blood 1994; 83:330-335; Reichel, M., et al.; Oncogene 2001; 20:2900-2907). Interestingly, several studies suggest that MLL-AF4 fusion oncogene supports cell survival in the t(4;11) context. Cells with t(4;11) translocation survive extended serum starvation (Kersey, J. H., et al.; Leukemia 1998; 12:1561-1564) and are resistant to CD95-mediated apoptosis (Dörrie, J., et al.; Leukemia 1999; 13:1539-1547).

To define the role of this fusion oncogene in leukemogenesis more precisely, we applied RNA interference (RNAi) to inhibit MLL-AF4 expression in leukemic cells. RNAi is a cellular process resulting in enzymatic cleavage and breakdown of mRNA, guided by sequence-specific double-stranded small interfering RNAs (siRNAs) (Dykxhoorn, D. M., et al.; Nat Rev Mol Cell Biol 2003; 4:457-467). Cell transfection with siRNAs results in the generation of a cytoplasmatically located ribonucleoprotein complex called RNA-induced silencing complex. Upon activation of this complex by discarding one of the siRNA strands (Khvorova, A., et al.; Cell 2003; 115:209-216; Schwarz, D. S., et al.; Cell 2003; 115:199-208), the remaining strand targets RISC to complementary RNA sequences leading to the endonucleolytic cleavage of the target RNA by the RISC component Ago-2 (Meister, G., et al.; Mol Cell 2004; 15:185-197; Rand, T. A., et al.; Proc Natl Acad Sci USA 2004; 101: 14385-14389; Song, J. J., et al.; Science 2004; 305:1434-1437). Exogenously added synthetic siRNAs were shown to act as very potent and sequence-specific agents to silence gene expression (Elbashir, S. M., et al.; Nature 2001; 411:494-498), demonstrating the great potential not only for the analysis of gene function but also for gene-specific therapeutic approaches (Cheng, J. C., Moore, T. B., and Sakamoto, K. M.; Mol Genet Metab 2003; 80:121-128; Heidenreich, O. Curr Pharm Biotechnol 2004; 5:349-354).

In the present study, we used RNAi to specifically inhibit MLL-AF4 gene expression in t(4;11) cells. We demonstrate that depletion of the fusion transcript MLL-AF4 inhibits clonogenicity and proliferation, induces apoptosis in t(4;11)-positive leukemic cells and compromizes their engraftment in a SCID mouse xenotransplantation model.

SUMMARY

The invention provides compositions and methods for reducing MLL-AF4 levels in a subject, e.g., a mammal, such as a human. The method includes administering to a subject an iRNA agent that reduces expression of an MLL-AF4 fusion gene (e.g., by at least 2%, 4%, 6%, 10%, 15%, 20% or greater) and/or inhibits the rate of proliferation of t(4; 11)-positive cells. The iRNA agent can be one described here, or can be a dsRNA that is based on one of the active sequences and target an identical region of an MLL-AF4 fusion gene, e.g., a mammalian MLL-AF4 fusion gene, such as an MLL-AF4 fusion gene from a human. The iRNA agent can comprise less than 30 nucleotides per strand, e.g., 21-23 nucleotides and consist of, comprise or be derived from one of the agents provided in Table 1, agent numbers 1-12. The double stranded iRNA agent can either have blunt ends or more preferably have overhangs of 1-4 nucleotides from one or both 3' ends of the agent. These preferred iRNA agents preferably include four or more nucleotide mismatches to all non-MLL-AF4 gene sequences in the subject.

In a first aspect, the invention specifically provides an iRNA agent comprising a sense strand, wherein the sense strand comprises a nucleotide sequence of at least 15 contiguous nucleotides from the sense strand sequences of agents 1-12 provided in Table 1 (SEQ ID NOs 5, 10, 12, 14, 18, 20, 22, 24, 26, 30, and 32), and an antisense strand, wherein the antisense strand comprises at least 15 contiguous nucleotides from the antisense sequences of agents 1-12 provided in Table 1 (SEQ ID NOs 6, 7, 11, 13, 15, 19, 21, 23, 25, 27, 31, and 33), e.g. agent number 5, sense strand sequence 5'-AAGAAAAGCAGACCUACUCCA-3' (SEQ ID NO:14), antisense strand sequence 5'-UGGAGUAGGU-CUGCUUUUCUUUU-3' (SEQ ID NO:15). The iRNA agents of Table 1, agent numbers 1-12, possess the advantageous and surprising ability to reduce the amount of MLL-AF4 mRNA present in cultured human SEM cells (leukemia cell line) after incubation with these agents by more than 40% compared to cells which have not been incubated with the agent (see FIG. 1).

In a second aspect, the invention provides an iRNA agent comprising a nucleotide sequence in the sense strand and a nucleotide sequence in the antisense strand each comprising a sequence of at least 16, 17 or 18 nucleotides which is essentially identical to one of the sequences of agents 1-12 of Table 1 (sense strand: SEQ ID NOs 5, 10, 12, 14, 18, 20, 22, 24, 26, 30, and 32; antisense strand: SEQ ID NOs 6, 7, 11, 13, 15, 19, 21, 23, 25, 27, 31, and 33), except that not more than 1, 2 or 3 nucleotides per strand, respectively, have been substituted by other nucleotides (e.g. adenosine replaced by uracil), while essentially retaining the ability to inhibit MLL-AF4 expression in cultured human SEM cells.

The iRNA agents of the invention may comprise a sense strand comprising at least 15 contiguous nucleotides from the sense strand sequences of agents 1, 2, 5, and 9 provided in Table 1 (SEQ ID NOs 5, 14, and 24), and an antisense strand comprising at least 15 contiguous nucleotides of the antisense sequences of agents 1, 2, 5, and 9 provided in Table 1 (SEQ ID NOs 6, 7, 15, and 25), wherein the iRNA agents reduce the amount of MLL-AF4 mRNA present in cultured human SEM cells after incubation with these agents by more than 60% compared to cells which have not been incubated with the agent. The antisense strand of the iRNA agents of the invention may be 30 or fewer nucleotides in length, and the duplex region of the iRNA agents may be 15-30 nucleotide pairs in length. The iRNA agents may comprise at least one nucleotide overhang having 1 to 4 unpaired nucleotides, preferably 2 or 3 unpaired nucleotides. The nucleotide overhang may be at the 3'-end of the antisense strand of the iRNA agent.

Furthermore, the iRNA agents of the invention may consist of (a) a double stranded structure formed by a sense strand having a nucleotide sequence chosen from the group of: the sequence of nucleotides of from position (5' to 3') 1 to 19, or 1 to 21, of the sense strand sequences SEQ ID NOs 5, 10, 12, 14, 18, 20, 22, 24, 26, 30, and 32, and an antisense strand having a nucleotide sequence chosen from the group of: the sequence of nucleotides of from positions (5' to 3') 1 to 21, or 3 to 21, of the antisense strand sequences SEQ ID NOs 6, 11, 13, 15, 19, 21, 23, 25, 27, 31, and 33, if the sense strand is chosen to have a sequence of nucleotides of from positions 1 to 21 of said sense strand sequences, and the sequence of nucleotides of from positions 3 to 21 of the antisense strand sequences SEQ ID NOs 6, 11, 13, 15, 19, 21, 23, 25, 27, 31, and 33, if the sense strand is chosen to have a sequence of nucleotides of from positions 1 to 19 of said sense strand sequences, (b) at least one single stranded overhang of 1 to 4 unpaired nucleotides at the 3'-end of the sense and/or antisense strand, wherein said single stranded overhang, if at the 3'-end of the sense strand, optionally comprises the nucleotides in positions 20 and 21 of the said sense strand sequences in their respective positions, and/or, if at the 3'-end of the antisense strand, optionally comprises the nucleotides in positions 22 and 23 of the said antisense strand sequences in their respective positions, wherein the iRNA agent does not comprise a single stranded overhang of 1 to 4 unpaired oligonucleotides on the 3'-end of the sense strand, if the double stranded structure is formed by a sense strand having a sequence of nucleotides of from position 1 to 21 of the said sense strand sequences and an antisense strand having a sequence of nucleotides of from position 1 to 21 of said antisense strand sequences. Specifically, the nucleotide sequence of the sense strand may consist of the nucleotide sequence of SEQ ID NO:14, and the nucleotide sequence of the antisense strand may consist of the nucleotide sequence of SEQ ID NO:14.

The iRNA agents of the invention are meant to reduce the amount of MLL-AF4 mRNA present in cultured human SEM cells after incubation with the iRNA agent by more than 40% compared to cells which have not been incubated with the agent. They may further comprise a modification that causes the iRNA agent to have increased stability in a biological sample, which may be a phosphorothioate or a 2'-modified nucleotide. For example, the iRNA agents may comprise at least one 5'-uridine-adenine-3' (5'-UA-3') dinucleotide wherein the uridine is a 2'-modified nucleotide; at least one 5'-uridine-guanine-3' (5'-UG-3') dinucleotide, wherein the 5'-uridine is a 2'-modified nucleotide; at least one 5'-cytidine-adenine-3' (5'-CA-3') dinucleotide, wherein the 5'-cytidine is a 2'-modified nucleotide; or at least one 5'-uridine-uridine-3' (5'-UU-3') dinucleotide, wherein the 5'-uridine is a 2'-modified nucleotide. The 2'-modification may be chosen from the group of: 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), and 2'-O—N-methylacetamido (2'-O-NMA).

The iRNA agents may further comprise a cholesterol moiety, which is preferably conjugated to the 3'-end of the sense strand of the iRNA agent. The iRNA agents may be targeted for uptake by cells of the liver or by cells of the gut.

In a third aspect, the invention provides a pharmaceutical composition, comprising:

(a) an iRNA agent of the invention; and
(b) a pharmaceutically acceptable carrier.

The pharmaceutical composition may further comprise a formulating agent which prolongs the half-life of the iRNA agent in human and/or mouse serum, or which facilitates uptake of the iRNA agent into cells. The formulating agent may comprise a polycation. Preferably, such pharmaceutical composition is useful in the treatment of a proliferative disordere.g. cancer, preferably leukemia, more preferably acute lymphoblastic leukemia. Preferably, the pharmaceutical composition is capable of reducing MLL-AF4 fusion gene expression in a cell or tissue of a subject (e.g., by at least 2%, 4%, 6%, 10%, 15%, 20% or greater) and/or of inhibiting the rate of proliferation of t(4;11)-positive cells upon administration of the pharmaceutical composition to the subject, e.g. a human.

In a fourth aspect, the invention provides a method of treating a human subject having or at risk for developing a proliferative disorder, comprising the step of: administering an iRNA agent of the invention to the human subject. The proliferative disorder is preferably cancer, and more preferably acute lymphoblastic leukemia. Therein, the iRNA agent may be administered in an amount sufficient to reduce the expression of MLL-AF4 in a cell or tissue of the subject (e.g., by at least 2%, 4%, 6%, 10%, 15%, 20% or greater) and/or of inhibiting the rate of proliferation of t(4;11)-positive cells.

In a fifth aspect, the invention provides a method of making a pharmaceutical composition, comprising the step of: formulating one of the iRNA agents of the invention with a pharmaceutical carrier, and optionally further comprises the step of: formulating the iRNA agent with a formulating agent which prolongs the half-life of the iRNA agent in human and/or mouse serum, or which facilitates uptake of the iRNA agent into cells. The formulating agent may comprise a polycation. The pharmaceutical composition of the inventive method is preferably useful in the treatment of a proliferative disorder, which is preferably cancer, more preferably a leukemia, and most preferably acute lymphoblastic leukemia. In one preferred embodiment, the pharmaceutical composition of he inventive method is capable of reducing MLL-AF4 fusion gene expression in a cell or tissue of a subject (e.g., by at least 2%, 4%, 6%, 10%, 15%, 20% or greater) and/or of inhibiting the rate of proliferation of t(4;11)-positive cells upon administration of the pharmaceutical composition to the subject, e.g. a human.

In a sixth aspect, the invention provides a method of reducing the amount of MLL-AF4 RNA in a cell (e.g., by at least 2%, 4%, 6%, 10%, 15%, 20% or greater) and/or of inhibiting the rate of proliferation of t(4;11)-positive cells, comprising the step of: contacting the cell with an iRNA agent of the invention. In one embodiment, the method is performed in vitro. Alternatively, the cell is a cell of a subject, and the subject is diagnosed as having a proliferative disorder, preferably cancer, and more preferably acute lymphoblastic leukemia. The cells can be located in a tumor, or they can be microclonal cells.

In a seventh aspect, the invention provides a method of making an iRNA agent of the invention, the method comprising the step of: synthesizing the sense and the antisense strand of the iRNA agent, wherein the sense and/or antisense strands comprise at least one nucleotide modification; said nucleotide modification is preferably a modification that causes the iRNA agent to have increased stability in a biological sample. Said method optionally further comprises the step of: administering the iRNA agent to a subject. In one embodiment, the subject is diagnosed as having a proliferative disorder, preferably cancer, and more preferably acute lymphoblastic leukemia. Therein, the subject may be a human.

TABLE 1

MLL-AF4 siRNA sequences[d].

| Agent No: | Strand ID: | Sequence[c] | SEQ ID NO: |
|---|---|---|---|
| 1 | MA3s[a] | 5' - AAAAG/CAGACCUACUCCAAUG - 3' | 5 |
|   | MA3as[b] | 3' - UCUUUUC/GUCUGGAUGAGGUUAC - 5' | 6 |
| 2 | MA3s | 5' - AAAAG/CAGACCUACUCCAAUG - 3' | 5 |
|   | MAxas | 3' - UCUUUUC/GUCUGGAUGAGGUU - 5' | 7 |
| 3 | MA4s | 5' - GAAAAG/CAGACCUACUCCAAU - 3' | 10 |
|   | MA4as | 3' - UUCUUUUC/GUCUGGAUGAGGUUA - 5' | 11 |
| 4 | MA5s | 5' - AGAAAAG/CAGACCUACUCCAA - 3' | 12 |
|   | MA5as | 3' - UUUCUUUUC/GUCUGGAUGAGGUU - 5' | 13 |
| 5 | MA6s | 5' - AAGAAAAG/CAGACCUACUCCA - 3' | 14 |
|   | MA6as | 3' - UUUUCUUUUC/GUCUGGAUGAGGU - 5' | 15 |
| 6 | MA8s | 5' - AAAAGAAAAG/CAGACCUACUC - 3' | 18 |
|   | MA8as | 3' - GGUUUUCUUUUC/GUCUGGAUGAG - 5' | 19 |
| 7 | MA9s | 5' - CAAAAGAAAAG/CAGACCUACU - 3' | 20 |
|   | MA9as | 3' - UGGUUUUCUUUUC/GUCUGGAUGA-5' | 21 |
| 8 | MA10s | 5' - CCAAAAGAAAAG/CAGACCUAC - 3' | 22 |
|   | MA10as | 3' - UUGGUUUUCUUUUC/GUCUGGAUG - 5' | 23 |
| 9 | MA11s | 5' - ACCAAAAGAAAAG/CAGACCUA - 3' | 24 |
|   | MA11as | 3' - UUUGGUUUUCUUUUC/GUCUGGAU - 5' | 25 |
| 10 | MA12s | 5' - AACCAAAAGAAAAG/CAGACCU - 3' | 26 |
|   | MA12as | 3' - UUUUGGUUUUCUUUUC/GUCUGGA - 5' | 27 |

TABLE 1-continued

MLL-AF4 siRNA sequences[d].

| Agent No: | Strand ID: | Sequence[c] | SEQ ID NO: |
|---|---|---|---|
| 11 | MA14s | 5' - AAAACCAAAAGAAAAG/CAGAC - 3' | 30 |
|  | MA14as | 3' - GUUUUUGGUUUUCUUUUC/GUCUG - 5' | 31 |
| 12 | siMARS | 5' - ACUUUAAGCAGACCUACUCCA - 3' | 32 |
|  |  | 3' - CCUGAAAUUCGUCUGGAUGAGGU - 5' | 33 |

[a]"s" indicates sense strand
[b]"as" indicates antisense strand
[c]"/" indicates the fusion between chromosome 11 and chromosome 4 sequence
[d]duplexed siRNA agents are referenced in the specification as "siMAxx"

In an eighth aspect, the invention provides a method of evaluating an iRNA agent thought to inhibit the expression of an MLL-AF4 gene, the method comprising:
 (a) providing an iRNA agent, wherein a first strand is sufficiently complementary to a nucleotide sequence of an MLL-AF4 mRNA, and a second strand is sufficiently complementary to the first strand to hybridize to the first strand;
 (b) contacting the iRNA agent to a cell comprising an MLL-AF4 gene;
 (c) comparing MLL-AF4 gene expression before contacting the iRNA agent to the cell, or of uncontacted control cells, to the MLL-AF4 gene expression after contacting the iRNA agent to the cell; and
 (d) determining whether the iRNA agent is useful for inhibiting MLL-AF4 gene expression, wherein the iRNA is useful if the amount of MLL-AF4 RNA present in the cell, or protein secreted by the cell, is less than the amount present or secreted prior to contacting the iRNA agent to the cell, or less than the amount present or secreted by cells not so contacted.

In one embodiment of this method, the iRNA agent is an iRNA agent of the invention as described above.

The iRNA agents can either contain only naturally occurring ribonucleotide subunits, or can be synthesized so as to contain one or more modifications to the sugar or base of one or more of the ribonucleotide subunits that is included in the agent. The iRNA agent can be further modified so as to be attached to a ligand that is selected to improve stability, distribution or cellular uptake of the agent, e.g. cholesterol. The agents can further be in isolated form or can be part of a pharmaceutical composition used for the methods described herein.

In another embodiment, and as described herein, a cholesterol moiety (e.g., on the 3'-end of the sense strand), a 2'-modification (e.g., a 2'-O-methyl or 2'-deoxy-2'-fluoro-modification), and a phosphorothioate (e.g., on the 3'-most one or two nucleotides of the sense and antisense strands) are present in the same iRNA agent.

Preferably, administration of an iRNA agent, e.g., an iRNA agent described herein, is for treatment of a disease or disorder present in the subject in which MLL-AF4 fusion gene expression plays a role. Administration of the iRNA agent may also be performed for prophylactic treatment of disorders mediated by the MLL-AF4 fusion.

The invention features preparations, including substantially pure or pharmaceutically acceptable preparations of iRNA agents which modulate e.g., inhibit, MLL-AF4. The iRNA agent that targets MLL-AF4 can be administered to a subject, wherein the subject is at risk for developing or having (e.g., diagnosed as having) a disorder characterized by the presence of the MLL-AF4 fusion gene, or other t(4;11) chromosomal translocations. The iRNA agent can be administered to an individual diagnosed with or having the disorder, or at risk for the disorder to delay onset of the disorder or a symptom of the disorder. These disorders include proliferative disorders, such as t(4;11)-associated leukemias, including acute lymphoblastic leukemias. For example, the iRNA agent that targets MLL-AF4 may be administered to a subject having (e.g., diagnosed as having) infant acute lymphoblastic leukemia, leucocytosis or an extramedullary disease in one or more organs (formation of blood cells outside of the bone marrow), e.g., the spleen, liver or lymph nodes.

The iRNA agent can also be targeted to a specific tissue such as the bone marrow, and MLL-AF4 expression levels in the tissue (e.g., in a tumor of the tissue) are decreased following administration of the MLL-AF4 iRNA agent. Preferably, the iRNA agent is modified to maximize the time the iRNA agent spends in the blood stream. For example, the iRNA agent can be associated with human serum albumin (HSA).

In the methods and compositions of the invention, the iRNA agent may be modified, or associated with a delivery agent, e.g., a delivery agent described herein, e.g., a liposome. Such modification may mediate association with a serum albumin (SA), e.g., a human serum albumin (HSA), or a fragment thereof, to increase the circulation time of the agent.

The present agents, methods and compositions utilize the cellular mechanisms involved in RNA interference to selectively degrade MLL-AF4 fusion mRNA in a cell. Therefore, the inventive methods will usually comprise a step of contacting a cell with one of the iRNA agents of the present invention. Such methods can be performed directly on a cell or can be performed on a mammalian subject by administering to a subject one of the iRNA agents of the present invention. In preferred embodiments, the cells are contacted with the iRNA agent at least twice, preferably at intervals of 48 hours. Reduction of MLL-AF4 fusion mRNA in a cell results in a reduction in the amount of MLL-AF4 fusion protein produced, and in an organism, may result in a decrease in MLL-AF4 fusion mediated disease effects.

The methods and compositions featured in the invention, e.g., the methods and compositions to treat the proliferative disorders described herein, can be used with any of the iRNA agents described. In addition, the methods and compositions featured in the invention can be used for the treatment of any disease or disorder described herein, and for the treatment of any subject, e.g., any animal, any mammal, such as any human.

The methods and compositions featured in the invention, e.g., the methods and iRNA compositions to treat the proliferative disorders described herein, can be used with any dosage and/or formulation described herein, as well as with any route of administration described herein.

The details of one or more embodiments featured in the invention are set forth in the accompanying drawings and the description below. Other features, objects, and advantages of the invention will be apparent from this description, the drawings, and from the claims. This application incorporates all cited references, patents, and patent applications by references in their entirety for all purposes.

BRIEF DESCRIPTION OF DRAWINGS

FIG. 1A: siRNA scan of the MLL-AF mRNA fusion site. MLL-AF4 mRNA levels normalized by GAPDH mRNA levels are shown. Target sites of the indicated siRNAs were moved by one single nucleotide from the AF4 part to the MLL part of the fusion site. Total RNA was isolated 24 h after electroporation with 500 nM of siRNA and analyzed by real time RT-PCR. Numbers on x-axis correspond to numbering of siRNAs in Table 2 (siMAn, n=1 to 14). Error bars show standard deviations. FIG. 1B: Time course of MLL-AF4 depletion. Total RNA was isolated at the indicated time points after mock electroporation, or electroporation with 750 nM siRNA siMA6 or the mismatch control siMAmm. Real time RT-PCR was performed as in FIG. 1A. FIG. 1C: Effects of the MLL-AF4 siRNA siMA6 and a mismatch control siMM on MLL-AF4, AF4 and MLL mRNA levels in SEM cells. Analysis was perfomed as in FIG. 1A. FIG. 1D: Depletion of MLL-AF4 protein upon siRNA transfection. Total cell lysates were isolated 48 h after mock electroporation, or electroporation with 500 nM siRNA siMA6 or mismatch control siMAmm. MLL-AF4 was detected with an antibody targeting the C-terminus of AF4. GAPDH served as a loading control and for normalization. Normalized MLL-AF4 protein levels are indicated at the bottom. FIG. 1E Effects of the MLL-AF4 siRNAs siMA6 and siMARS and a mismatch control siMM on MLL-AF4, AF4 and MLL mRNA levels in RS4;11 cells. Analysis was performed as in FIG. 1A. siMA6 is homologous to the MLL-AF4 variant expressed in SEM cells, siMARS targets the variant present in RS4;11 cells. FIG. 1F: MLL-AF4 siRNAs do not induce an interferon response. SEM cells were transfected with the indicated RNAs. PolyIC (7.5 μg/mg) served as a positive control for the induction of the interferon response genes OAS1 and STAT1. Analysis was performed as in FIG. 1A.

FIGS. 2A-2E. MLL-AF4 depletion inhibits colony formation and proliferation of t(4;11)-positive leukemic cells. FIG. 2A: Specificity of MLL-AF4 and AML1/MTG8 siRNAs. SEM cells express MLL-AF4, whereas Kasumi-1 cells express AML1/MTG8. The number of colonies formed by siMA6-treated SEM or siAGF 1-treated Kasumi-1 cells are significantly lower than those of cells treated with the respective mismatch controls (p<0.001). FIG. 2B: Inhibition of RS4;11 clonogenicity is dependent on perfect homology to the MLL-AF4 fusion site. The number of colonies formed by siMARS treated RS4;11 cells is significantly lower than by mock-treated RS4;11 cells, RS4;11 cells treated with the e9-e4-variant-specific siMA6, or the e9-e4 mismatch control siMAmm (p<0.0001). FIG. 2C: siRNAs targeting MLL-AF4 do not affect colony formation of primary human CD34+ hemopoetic cells. Primary human CD34+ hemopoetic cell were electroporated with 750 nM siMA6 (siRNA targeting MLL-AF4 e9-e4 variant expressed in SEM cells), siMARS (siRNA targeting MLL-AF4 e10-e4 variant expressed in RS4;11 cells), or the e9-e4 mismatch control siMM. Error bars show standard deviations. FIG. 2D: Growth curves of siRNA-treated SEM and RS4;11 cells. Every second day, cells were mock electroporated or electroporated with 750 nM siMA6, siMARS, or the mismatch control siMAmm. Cell numbers were determined using the MTT assay. Only the siRNA having complementarity to the fusion site variant present in the respective cell line was able to suppress growth. Error bars indicate standard deviations. FIG. 2E: Effects of MLL-AF4 siRNAs on the cell cycle distribution of SEM and RS4;11 cells. The graphs show the percentage of cells in the indicated cycle phase. Cell cycle distribution was determined by flow cytometry at the indicated days using cells from the time course experiments shown in FIG. 2D.

FIG. 3A: Effects of MLL-AF4 suppression on the fraction of sub G1 cells. Cells obtained from the time courses shown in FIGS. 2D and 2E were analyzed for DNA content by flow cytometry. FIG. 3B: Annexin V staining of SEM cells. Annexin V-positive SEM cells were quantified by flow cytometry 4 days after the second electroporation with 750 nM of the indicated siRNA. The percentages of annexin V and annexin V/propidium iodide-positive cells are given in the corresponding quadrants. FIG. 3C: MLL-AF4 suppression triggers caspase-3 activation and diminishes Bcl-XL protein levels. Immunoblots show proteolytically activated caspase-3 and Bcl-XL proteins. Tubulin and GAPDH served as loading controls.

FIG. 5A: Survival curves of SCID mice transplanted with SEM cells. Prior to transplantation, SEM cells were either mock electroporated twice, or elactroporated twice with with siRNAs siMA 6 or its mismatch control siMAmm. Pretreatment with the MLL-AF4 e9-e4-specific siRNA siMA6 extended median survival and increased overall survival significantly compared to mock or control siRNA pretreatment (p<0.01 according to log-rank test). FIG. 5B: FACS analysis of bone marrow. Bone marrow cells of animals were stained with anti-human CD45 antibody and analyzed by flow cytometry. Animals treated with siMA6 had considerably lower CD45 positive cell counts. FIG. 5C: Liver and spleen histologies. Original magnification 200×; scale bar, 50 μm. Mice transplanted with mock or siMM-pretreated cells were moribund at the time of analysis. The animal transplanted with siMA6-pretreated cells was sacrificed 228 days after transplantation without any sign of leukemia-associated morbidity. FIG. 5D: Comparison of spleen size. The spleen on the left stems from a mock treated animal, the spleen in the middle from an animal treated with the mismatch control siRNA siMM, the right spleen from an animal treated with siRNA siMA6 specific for MLL-AF4. FIG. 5E: Graphical representation of organ weights. Organ weights were normalized to whole body weight. Normalized liver and spleen weights of surviving animals of the siMA6 group were significantly smaller than those from the mock or siMM mismatch control group (p<0.05 and p<0.001, respectively).

DETAILED DESCRIPTION

Figure 1A:
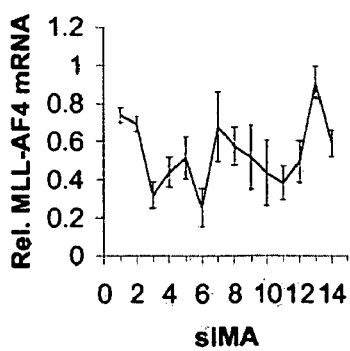
FIGS. 1A-1F. Activity and specificity of MLL-AF4 siRNAs.

For ease of exposition the term "nucleotide" or "ribonucleotide" is sometimes used herein in reference to one or more monomeric subunits of an RNA agent. It will be understood that the usage of the term "ribonucleotide" or "nucleotide" herein can, in the case of a modified RNA or nucleotide surrogate, also refer to a modified nucleotide, or surrogate replacement moiety, as further described below, at one or more positions.

An "RNA agent" as used herein, is an unmodified RNA, modified RNA, or nucleoside surrogate, all of which are described herein. While numerous modified RNAs and nucleoside surrogates are described, preferred examples include those which have greater resistance to nuclease degradation than do unmodified RNAs. Preferred examples include those that have a 2' sugar modification, a modification in a single strand overhang, preferably a 3' single strand overhang, or, particularly if single stranded, a 5'-modification which includes one or more phosphate groups or one or more analogs of a phosphate group.

An "iRNA agent" (abbreviation for "interfering RNA agent") as used herein, is an RNA agent, which can downregulate the expression of a target gene, such as the target fusion gene, MLL-AF4. While not wishing to be bound by theory, an iRNA agent may act by one or more of a number of mechanisms, including post-transcriptional cleavage of a target mRNA sometimes referred to in the art as RNAi, or pre-transcriptional or pre-translational mechanisms. An iRNA agent can be a double stranded iRNA agent.

A "ds iRNA agent" (abbreviation for "double stranded iRNA agent"), as used herein, is an iRNA agent which includes more than one, and preferably two, strands in which interstrand hybridization can form a region of duplex structure. A "strand" herein refers to a contigouous sequence of nucleotides (including non-naturally occurring or modified nucleotides). The two or more strands may be, or each form a part of, separate molecules, or they may be covalently interconnected, e.g. by a linker, e.g. a polyethyleneglycol linker, to form but one molecule. At least one strand can include a region which is sufficiently complementary to a target RNA. Such strand is termed the "antisense strand". A second strand comprised in the dsRNA agent which comprises a region complementary to the antisense strand is termed the "sense strand". However, a ds iRNA agent can also be formed from a single RNA molecule which is, at least partly; self-complementary, forming, e.g., a hairpin or panhandle structure, including a duplex region. In such case, the term "strand" refers to one of the regions of the RNA molecule that is complementary to another region of the same RNA molecule.

Although, in mammalian cells, long ds iRNA agents can induce the interferon response which is frequently deleterious, short ds iRNA agents do not trigger the interferon response, at least not to an extent that is deleterious to the cell and/or host (Manche, L., et al., Mol. Cell. Biol. 1992, 12:5238; Lee. S B, Esteban, M, Virology 1994, 199:491; Castelli, J C, et al., J. Exp. Med. 1997, 186:967; Zheng, X., Bevilacqua, P C, RNA 2004, 10:1934; Heidel et al., Nature Biotechn. 2004, 22:1579). The iRNA agents of the present invention include molecules which are sufficiently short that they do not trigger a deleterious non-specific interferon response in normal mammalian cells. Thus, the administration of a composition of an iRNA agent (e.g., formulated as described herein) to a subject can be used to silence expression of the MLL-AF4 fusion gene in MLL-AF4 fusion expressing cells comprised in the subject, while circumventing an interferon response. Molecules that are short enough that they do not trigger a deleterious interferon response are termed siRNA agents or siRNAs herein. "siRNA agent" or "siRNA" as used herein, refers to an iRNA agent, e.g., a ds iRNA agent, that is sufficiently short that it does not induce a deleterious interferon response in a human cell, e.g., it has a duplexed region of less than 60 but preferably less than 50, 40, or 30 nucleotide pairs.

The isolated iRNA agents described herein, including ds iRNA agents and siRNA agents, can mediate silencing of an MLL-AF4 fusion gene, e.g., by RNA degradation. For convenience, such RNA is also referred to herein as the RNA to be silenced. Such a gene is also referred to as a target gene. Preferably, the RNA to be silenced is a gene product of an MLL-AF4 gene fusion that is endogenous to the cell, e.g. a leukemic cell.

As used herein, the phrase "mediates RNAi" refers to the ability of an agent to silence, in a sequence specific manner, a target gene. "Silencing a target gene" means the process whereby a cell containing and/or secreting a certain product of the target gene when not in contact with the agent, will contain and/or secret at least 10%, 20%, 30%, 40%, 50%, 60%, 70%, 80%, or 90% less of such gene product when contacted with the agent, as compared to a similar cell which has not been contacted with the agent. Such product of the target gene can, for example, be a messenger RNA (mRNA), a protein, or a regulatory element.

As used herein, "the term "complementary" is used to indicate a sufficient degree of complementarity such that stable and specific binding occurs between a compound featured in the invention and a target RNA molecule, e.g. an MLL-AF4 mRNA molecule. Specific binding requires a sufficient degree of complementarity to avoid non-specific binding of the oligomeric compound to non-target sequences under conditions in which specific binding is desired, i.e., under physiological conditions in the case of in vivo assays or therapeutic treatment, or in the case of in vitro assays, under conditions in which the assays are performed. The non-target sequences typically differ by at least four nucleotides.

As used herein, an iRNA agent is "sufficiently complementary" to a target RNA, e.g., a target mRNA (e.g., a target MLL-AF4 mRNA) if the iRNA agent reduces the production of a protein encoded by the target RNA in a cell. The iRNA agent may also be "exactly complementary" (excluding the SRMS containing subunit(s)) to the target RNA, e.g., the target RNA and the iRNA agent anneal, preferably to form a hybrid made exclusively of Watson-Crick basepairs in the region of exact complementarity. A "sufficiently complementary" iRNA agent can include an internal region (e.g., of at least 10 nucleotides) that is exactly complementary to a target MLL-AF4 RNA. Moreover, in some embodiments, the iRNA agent specifically discriminates a single-nucleotide difference. In this case, the iRNA agent only mediates RNAi if exact complementary is found in the region (e.g., within 7 nucleotides of) the single-nucleotide difference. Prefered iRNA agents will be based on or consist or comprise the sense and antisense sequences provided in Table 1.

As used herein, "essentially identical" when used referring to a first nucleotide sequence in comparison to a second nucleotide sequence means that the first nucleotide sequence is identical to the second nucleotide sequence except for up to one, two or three nucleotide substitutions (e.g., adenosine replaced by uracil). "Essentially retaining the ability to inhibit MLL-AF4 expression in cultured human SEM cells" as used herein referring to an iRNA agent not identical to but derived from one of the iRNA agents of Table 1 by deletion, addition or substitution of nucleotides, means that the derived iRNA agent possesses an inhibitory activity lower by not more than 20% inhibition compared to the iRNA agent of Table 1 it was derived from. For example, an iRNA agent derived from an iRNA agent of Table 1, which lowers the amount of MLL-AF4 mRNA present in cultured human SEM cells by 40% may itself lower the amount of MLL-AF4 mRNA present in cultured human SEM cells by at least 40% in order to be considered as essentially retaining the ability to inhibit MLL-AF4 expression in cultured human SEM cells. Optionally, an iRNA agent featured in the invention may lower the amount of MLL-AF4 mRNA present in cultured human SEM cells, by at least 40%.

As used herein, a "subject" refers to a mammalian organism undergoing treatment for a disorder mediated by MLL-AF4 fusion protein expression. The subject can be any mammal, such as a cow, horse, mouse, rat, dog, pig, goat, or a primate. In the preferred embodiment, the subject is a human.

As used herein, disorders associated with MLL-AF4 fusion expression refers to any biological or pathological state that 1) is mediated in part by the presence of MLL-AF4 fusion protein and 2) whose outcome can be affected by reducing the level of MLL-AF4 fusion protein present. Specific disorder associated with MLL-AF4 fusion expression are noted below.

Disorders Associated with MML-AF4 Misexpression

The MLL-AF4 fusion product has been associated with acute lymphoblastic leukemias (ALLs), such as infant acute lymphoblastic leukemia. Patients having an ALL typically present marked leucocytosis and extramedullary disease in multiple organs, respond poorly to chemotherapy and have poor prognosis.

Design and Selection of iRNA Agents

The present invention is based on the demonstration of silencing of an MLL-AF4 fusion gene in vitro in cultured cells after incubation with an iRNA agent, and the resulting antiproliferative effect.

An iRNA agent can be rationally designed based on sequence information and desired characteristics. For example, an iRNA agent can be designed according to the relative melting temperature of the candidate duplex. Generally, the duplex should have a lower melting temperature at the 5' end of the antisense strand than at the 3' end of the antisense strand.

Candidate iRNA agents can also be designed by performing, for example, a gene walk analysis of the genes that will serve as the target gene. Overlapping, adjacent, or closely spaced candidate agents corresponding to all or some of the transcribed region can be generated and tested. Each of the iRNA agents can be tested and evaluated for the ability to down regulate the target gene expression (see below, "Evaluation of Candidate iRNA agents").

Example 1 herein below shows a gene walk approach was used to evaluate potential iRNA agents targeting the fusion site of human MLL-AF4 mRNA. Based on the results provided, Table 1 provides active iRNA agents targeting MLL-AF4. As shown in the Examples below, the iRNA agents of Table 1, agent numbers 1-12, possess the advantageous and surprising ability to reduce the amount of MLL-AF4 fusion mRNA present in cultured MLL-AF4 fusion gene expressing cells after incubation with these agents by more than 40% compared to cells which have not been incubated with the agent.

Based on these results, the invention specifically provides an iRNA agent that includes a sense strand having at least 15 contiguous nucleotides of the sense strand sequences of the agents provided in Table 1, and an antisense strand having at least 15 contiguous nucleotides of the antisense sequences of the agents provided in Table 1 under agent numbers 1-12.

The iRNA agents shown in Example 1 hereinbelow, except for agent number 2, are composed of a sense strand of 21 nucleotides in length, and an antisense strand of 23 nucleotides in length. However, while these lengths may potentially be optimal, the iRNA agents are not meant to be limited to these lengths. The skilled person is well aware that shorter or longer iRNA agents may be similarly effective, since, within certain length ranges, the efficacy is rather a function of the nucleotide sequence than strand length. For example, Yang, D., et al., PNAS 2002, 99:9942-9947, demonstrated similar efficacies for iRNA agents of lengths between 21 and 30 base pairs. Others have shown effective silencing of genes by iRNA agents down to a length of approx. 15 base pairs (Byrom, W. M., et al., Inducing RNAi with siRNA Cocktails Generated by RNase III; Tech Notes 10(1), Ambion, Inc., Austin, Tex., USA).

Therefore, it is possible and contemplated by the instant invention to select from the sequences provided in Table 1 a partial sequence of between 15 to 22 nucleotides for the generation of an iRNA agent derived from one of the sequences provided in Table 1. Alternatively, one may add one or several nucleotides to one of the sequences provided in Table 1, preferably, but not necessarily, in such a fashion that the added nucleotides are complementary to the respective sequence of the target gene, e.g. an MLL-AF4 fusion gene. All such derived iRNA agents are included in the iRNA agents of the present invention, provided they essentially retain the ability to inhibit MLL-AF4 expression in cultured human SEM cells.

The antisense strand of an iRNA agent should be equal to or at least, 14, 15, 16 17, 18, 19, 25, 29, 40, or 50 nucleotides in length. It should be equal to or less than 60, 50, 40, or 30, nucleotides in length. Preferred ranges are 15-30, 17 to 25, 19 to 23, and 19 to 21 nucleotides in length.

The sense strand of an iRNA agent should be equal to or at least 14, 15, 16 17, 18, 19, 25, 29, 40, or 50 nucleotides in length. It should be equal to or less than 60, 50, 40, or 30 nucleotides in length. Preferred ranges are 15-30, 17 to 25, 19 to 23, and 19 to 21 nucleotides in length.

The double stranded portion of an iRNA agent should be equal to or at least, 15, 16 17, 18, 19, 20, 21, 22, 23, 24, 25, 29, 40, or 50 nucleotide pairs in length. It should be equal to or less than 60, 50, 40, or 30 nucleotides pairs in length. Preferred ranges are 15-30, 17 to 25, 19 to 23, and 19 to 21 nucleotides pairs in length.

Generally, the iRNA agents of the instant invention include a region of sufficient complementarity to the MLL-AF4 fusion gene, and are of sufficient length in terms of nucleotides, that the iRNA agent, or a fragment thereof, can mediate down regulation of the MLL-AF4 fusion gene. The antisense strands of the iRNA agents of Table 1, are fully complementary to the mRNA sequences of human MLL-AF4 fusion gene, and their sense strands are fully complementary to the antisense strands except for the two 3'-terminal nucleotides on the antisense strand. However, it is not necessary that there be perfect complementarity between the iRNA agent and the target, but the correspondence must be sufficient to enable the iRNA agent, or a cleavage product thereof, to direct sequence specific silencing, e.g., by RNAi cleavage of an MLL-AF4 mRNA.

Therefore, the iRNA agents of the instant invention include agents comprising a sense strand and antisense strand each comprising a sequence of at least 16, 17 or 18 nucleotides which is essentially identical, as defined below, to one of the sequences of Table 1, except that not more than 1, 2 or 3 nucleotides per strand, respectively, have been substituted by other nucleotides (e.g. adenosine replaced by uracil), while essentially retaining the ability to inhibit MLL-AF4 expression in cultured human SEM cells, as defined below. These agents will therefore possess at least 15 nucleotides identical to one of the sequences of Table 1, but 1, 2 or 3 base mismatches with respect to either the target MLL-AF4 mRNA sequence or between the sense and antisense strand are introduced. Mismatches to the target MLL-AF4 mRNA sequence, particularly in the antisense strand, are most tolerated in the terminal regions and if present are preferably in a terminal region or regions, e.g., within 6, 5, 4, or 3 nucleotides of a 5' and/or 3' terminus, most preferably within 6, 5, 4, or 3 nucleotides of the 5'-terminus of the sense strand or the 3'-terminus of the antisense strand. The sense strand need only be sufficiently complementary with the antisense strand to maintain the overall double stranded character of the molecule.

It is preferred that the sense and antisense strands be chosen such that the iRNA agent includes a single strand or unpaired region at one or both ends of the molecule. Thus, an iRNA agent contains sense and antisense strands, preferably paired to contain an overhang, e.g., one or two 5' or 3' overhangs but preferably a 3' overhang of 2-3 nucleotides. Most embodiments will have a 3' overhang. Preferred siRNA agents will have single-stranded overhangs, preferably 3' overhangs, of 1 to 4, or preferably 2 or 3 nucleotides, in length at each end. The overhangs can be the result of one strand being longer than the other, or the result of two strands of the same length being staggered. 5'-ends are preferably phosphorylated.

Preferred lengths for the duplexed region is between 15 and 30, most preferably 18, 19, 20, 21, 22, and 23 nucleotides in length, e.g., in the siRNA agent range discussed above. siRNA agents can resemble in length and structure the natural Dicer processed products from long dsRNAs. Embodiments in which the two strands of the siRNA agent are linked, e.g., covalently linked are also included. Hairpin, or other single strand structures which provide the required double stranded region, and preferably a 3' overhang are also within the invention.

Evaluation of Candidate iRNA Agents

A candidate iRNA agent can be evaluated for its ability to downregulate target gene expression. For example, a candidate iRNA agent can be provided, and contacted with a cell, e.g. an SEM cell, that expresses the target gene, e.g., the MLL-AF4 fusion gene, either endogenously or because it has been transfected with a construct from which the MLL-AF4 fusion gene can be expressed. The level of target gene expression prior to and following contact with the candidate iRNA agent can be compared, e.g., on an mRNA or protein level. If it is determined that the amount of RNA or protein expressed from the target gene is lower following contact with the iRNA agent, then it can be concluded that the iRNA agent downregulates target gene expression. The level of target MLL-AF4 RNA or MLL-AF4 protein in the cell can be determined by any method desired. For example, the level of target RNA can be determined by Northern blot analysis, reverse transcription coupled with polymerase chain reaction (RT-PCR), or RNAse protection assay. The level of protein can be determined, for example, by Western blot analysis or immuno-fluorescence.

Stability Testing, Modification, and Retesting of iRNA Agents

A candidate iRNA agent can be evaluated with respect to stability, e.g, its susceptibility to cleavage by an endonuclease or exonuclease, such as when the iRNA agent is introduced into the body of a subject. Methods can be employed to identify sites that are susceptible to modification, particularly cleavage, e.g., cleavage by a component found in the body of a subject.

When sites susceptible to cleavage are identified, a further iRNA agent can be designed and/or synthesized wherein the potential cleavage site is made resistant to cleavage, e.g. by introduction of a 2'-modification on the site of cleavage, e.g., a 2'-O-mathyl group. This further iRNA agen can be retested for stability, and this process may be iterated until an iRNA agent is found exhibiting the desired stability.

In Vivo Testing

An iRNA agent identified as being capable of inhibiting MLL-AF4 gene expression can be tested for functionality in vivo in an animal model (e.g., in a mammal, such as in mouse or rat). For example, the iRNA agent can be administered to an animal, e.g., an animal engineered to express the MLL-AF4 gene fusion, and the iRNA agent evaluated with respect to its biodistribution, stability, and its ability to inhibit MLL-AF4 gene expression.

The iRNA agent can be administered directly to the target tissue, such as by injection, or the iRNA agent can be administered to the animal model in the same manner that it would be administered to a human The iRNA agent can also be evaluated for its intracellular distribution. The evaluation can include determining whether the iRNA agent was taken up into the cell. The evaluation can also include determining the stability (e.g., the half-life) of the iRNA agent. Evaluation of an iRNA agent in vivo can be facilitated by use of an iRNA agent conjugated to a traceable marker (e.g., a fluorescent marker such as fluorescein; a radioactive label, such as $^{35}$S, $^{32}$P, $^{33}$P, or $^3$H; gold particles; or antigen particles for immunohistochemistry).

The iRNA agent can be evaluated with respect to its ability to down regulate MLL-AF4 gene expression. Levels of MLL-AF4 gene expression in vivo can be measured, for example, by in situ hybridization, or by the isolation of RNA from tissue prior to and following exposure to the iRNA agent. Where the animal needs to be sacrificed in order to harvest the tissue, an untreated control animal will serve for comparison. Target MLL-AF4 mRNA can be detected by any desired method, including but not limited to RT-PCR, Northern blot, branched-DNA assay, or RNAase protection assay. Alternatively, or additionally, MLL-AF4 gene expression can be monitored by performing Western blot analysis on tissue extracts treated with the iRNA agent.

iRNA Chemistry

Described herein are isolated iRNA agents, e.g., dsRNA agents, that mediate RNAi to inhibit expression of MLL-AF4.

RNA agents discussed herein include otherwise unmodified RNA as well as RNA which have been modified, e.g., to improve efficacy, and polymers of nucleoside surrogates. Unmodified RNA refers to a molecule in which the components of the nucleic acid, namely sugars, bases, and phosphate moieties, are the same or essentially the same as that which occur in nature, preferably as occur naturally in the human body. The art has referred to rare or unusual, but naturally occurring, RNAs as modified RNAs, see, e.g., Limbach et al., (1994) *Nucleic Acids Res.* 22: 2183-2196. Such rare or unusual RNAs, often termed modified RNAs (apparently because the are typically the result of a post-transcriptional modification) are within the term unmodified RNA, as used herein. Modified RNA as used herein refers to a molecule in which one or more of the components of the nucleic acid, namely sugars, bases, and phosphate moieties, are different from that which occur in nature, preferably different from that which occurs in the human body. While they are referred to as modified "RNAs," they will of course, because of the modification, include molecules which are not RNAs. Nucleoside surrogates are molecules in which the ribophosphate backbone is replaced with a non-ribophosphate construct that allows the bases to the presented in the correct spatial relationship such that hybridization is substantially similar to what is seen with a ribophosphate backbone, e.g., non-charged mimics of the ribophosphate backbone. Examples of all of the above are discussed herein.

Modifications described herein can be incorporated into any double-stranded RNA and RNA-like molecule described herein, e.g., an iRNA agent. It may be desirable to modify one or both of the antisense and sense strands of an iRNA agent. As nucleic acids are polymers of subunits or monomers, many of the modifications described below occur at a position which is repeated within a nucleic acid, e.g., a modification of a base, or a phosphate moiety, or the non-linking O of a phosphate moiety. In some cases the modification will occur at all of the subject positions in the nucleic acid but in many, and in fact in most, cases it will not. By way of example, a modification may only occur at a 3' or 5' terminal position, may only occur in a terminal region, e.g. at a position on a terminal nucleotide or in the last 2, 3, 4, 5, or 10 nucleotides of a strand. A modification may occur in a double strand region, a single strand region, or in both. E.g., a phosphorothioate modification at a non-linking O position may only occur at one or both termini, may only occur in a terminal regions, e.g., at a position on a terminal nucleotide or in the last 2, 3, 4, 5, or 10 nucleotides of a strand, or may occur in double strand and single strand regions, particularly at termini. Similarly, a modification may occur on the sense strand, antisense strand, or both. In some cases, the sense and antisense strand will have the same modifications or the same class of modifications, but in other cases the sense and antisense strand will have different modifications, e.g., in some cases it may be desirable to modify only one strand, e.g. the sense strand.

Two prime objectives for the introduction of modifications into iRNA agents is their stabilization towards degradation in biological environments and the improvement of pharmacological properties, e.g. pharmacodynamic properties, which are further discussed below. Other suitable modifications to a sugar, base, or backbone of an iRNA agent are described in co-owned PCT Application No. PCT/US2004/01193, filed Jan. 16, 2004. An iRNA agent can include a non-naturally occurring base, such as the bases described in co-owned PCT Application No. PCT/US2004/011822, filed Apr. 16, 2004. An iRNA agent can include a non-naturally occurring sugar, such as a non-carbohydrate cyclic carrier molecule. Exemplary features of non-naturally occurring sugars for use in iRNA agents are described in co-owned PCT Application No. PCT/US2004/11829 filed Apr. 16, 2003.

An iRNA agent can include an internucleotide linkage (e.g., the chiral phosphorothioate linkage) useful for increasing nuclease resistance. In addition, or in the alternative, an iRNA agent can include a ribose mimic for increased nuclease resistance. Exemplary internucleotide linkages and ribose mimics for increased nuclease resistance are described in co-owned PCT Application No. PCT/US2004/07070 filed on Mar. 8, 2004.

An iRNA agent can include ligand-conjugated monomer subunits and monomers for oligonucleotide synthesis. Exemplary monomers are described in co-owned U.S. application Ser. No. 10/916,185 pending, filed on Aug. 10, 2004.

An iRNA agent can have a ZXY structure, such as is described in co-owned PCT Application No. PCT/US2004/07070 filed on Mar. 8, 2004.

An iRNA agent can be complexed with an amphipathic moiety. Exemplary amphipathic moieties for use with iRNA agents are described in co-owned PCT Application No. PCT/US2004/07070 filed on Mar. 8, 2004.

The sense and antisense sequences of an iRNA agent can be palindromic. Exemplary features of palindromic iRNA agents are described in co-owned PCT Application No.PCT/US2004/07070 filed on Mar. 8, 2004.

In another embodiment, the iRNA agent can be complexed to a delivery agent that features a modular complex. The complex can include a carrier agent linked to one or more of (preferably two or more, more preferably all three of): (a) a condensing agent (e.g., an agent capable of attracting, e.g., binding, a nucleic acid, e.g., through ionic or electrostatic interactions); (b) a fusogenic agent (e.g., an agent capable of fusing and/or being transported through a cell membrane); and (c) a targeting group, e.g., a cell or tissue targeting agent, e.g., a lectin, glycoprotein, lipid or protein, e.g., an antibody, that binds to a specified cell type. iRNA agents complexed to a delivery agent are described in co-owned PCT Application No. PCT/US2004/07070 filed on Mar. 8, 2004.

An iRNA agent can have non-canonical pairings, such as between the sense and antisense sequences of the iRNA duplex. Exemplary features of non-canonical iRNA agents are described in co-owned PCT Application No. PCT/US2004/07070 filed on Mar. 8, 2004.

Enhanced Nuclease Resistance

An iRNA agent, e.g., an iRNA agent that targets MLL-AF4 fusion, can have enhanced resistance to nucleases.

One way to increase resistance is to identify cleavage sites and modify such sites to inhibit cleavage, as described in co-owned U.S. Application No. 60/559,917, filed on May 4, 2004. For example, the dinucleotides 5'-UA-3', 5'-UG-3', 5'-CA-3', 5'-UU-3', or 5'-CC-3' can serve as cleavage sites. In certain embodiments, all the pyrimidines of an iRNA agent carry a 2'-modification, and the iRNA agent therefore has enhanced resistance to endonucleases. Enhanced nuclease resistance can also be achieved by modifying the 5' nucleotide, resulting, for example, in at least one 5'-uridine-adenine-3' (5'-UA-3') dinucleotide wherein the uridine is a 2'-modified nucleotide; at least one 5'-uridine-guanine-3' (5'-UG-3') dinucleotide, wherein the 5'-uridine is a 2'-modified nucleotide; at least one 5'-cytidine-adenine-3' (5'-CA-3') dinucleotide, wherein the 5'-cytidine is a 2'-modified nucleotide; at least one 5'-uridine-uridine-3' (5'-UU-3') dinucleotide, wherein the 5'-uridine is a 2'-modified nucleotide; or at least one 5'-cytidine-cytidine-3' (5'-CC-3') dinucleotide, wherein the 5'-cytidine is a 2'-modified nucleotide, as described in co-owned U.S. Application No. 60/574,744, filed on May 27, 2004. The iRNA agent can include at least 2, at least 3, at least 4 or at least 5 of such dinucleotides.

Preferably, the 2'-modified nucleotides include, for example, a 2'-modified ribose unit, e.g., the 2'-hydroxyl group (OH) can be modified or replaced with a number of different "oxy" or "deoxy" substituents.

Examples of "oxy"-2' hydroxyl group modifications include alkoxy or aryloxy (OR, e.g., R=H, alkyl, cycloalkyl, aryl, aralkyl, heteroaryl or sugar); polyethyleneglycols (PEG), $O(CH_2CH_2O)_nCH_2CH_2OR$; "locked"

nucleic acids (LNA) in which the 2' hydroxyl is connected, e.g., by a methylene bridge, to the 4' carbon of the same ribose sugar; O-AMINE and aminoalkoxy, $O(CH_2)_n$AMINE, (e.g., AMINE=$NH_2$; alkylamino, dialkylamino, heterocyclyl amino, arylamino, diaryl amino, heteroaryl amino, or diheteroaryl amino, ethylene diamine, polyamino). It is noteworthy that oligonucleotides containing only the methoxyethyl group (MOE), ($OCH_2CH_2OCH_3$, a PEG derivative), exhibit nuclease stabilities comparable to those modified with the robust phosphorothioate modification.

"Deoxy" modifications include hydrogen (i.e. deoxyribose sugars, which are of particular relevance to the overhang portions of partially ds RNA); halo (e.g., fluoro); amino (e.g. $NH_2$; alkylamino, dialkylamino, heterocyclyl, arylamino, diaryl amino, heteroaryl amino, diheteroaryl amino, or amino acid); $NH(CH_2CH_2NH)_nCH_2CH_2$-AMINE (AMINE=$NH_2$; alkylamino, dialkylamino, heterocyclyl amino, arylamino, diaryl amino, heteroaryl amino, or diheteroaryl amino), —NHC(O)R(R=alkyl, cycloalkyl, aryl, aralkyl, heteroaryl or sugar), cyano; mercapto; alkyl-thioalkyl; thioalkoxy; and alkyl, cycloalkyl, aryl, alkenyl and alkynyl, which may be optionally substituted with e.g., an amino functionality.

Preferred substitutents are 2'-methoxyethyl, 2'-$OCH_3$, 2'-O-allyl, 2'-C— allyl, and 2'-fluoro.

The inclusion of furanose sugars in the oligonucleotide backbone can also decrease endonucleolytic cleavage. An iRNA agent can be further modified by including a 3' cationic group, or by inverting the nucleoside at the 3'-terminus with a 3'-3' linkage. In another alternative, the 3'-terminus can be blocked with an aminoalkyl group, e.g., a 3'C5-aminoalkyl dT. Other 3' conjugates can inhibit 3'-5' exonucleolytic cleavage. While not being bound by theory, a 3' conjugate, such as naproxen or ibuprofen, may inhibit exonucleolytic cleavage by sterically blocking the exonuclease from binding to the 3'-end of oligonucleotide. Even small alkyl chains, aryl groups, or heterocyclic conjugates or modified sugars (D-ribose, deoxyribose, glucose etc.) can block 3'-5'-exonucleases.

Nucleolytic cleavage can also be inhibited by the introduction of phosphate linker modifications, e.g., phosphorothioate linkages. Thus, preferred iRNA agents include nucleotide dimers enriched or pure for a particular chiral form of a modified phosphate group containing a heteroatom at a nonbridging position normally occupied by oxygen. The heteroatom can be S, Se, $Nr_2$, or $Br_3$. When the heteroatom is S, enriched or chirally pure Sp linkage is preferred. Enriched means at least 70, 80, 90, 95, or 99% of the preferred form. Modified phosphate linkages are particularly efficient in inhibiting exonucleolytic cleavage when introduced near the 5'- or 3'-terminal positions, and preferably the 5'-terminal positions, of an iRNA agent.

5' conjugates can also inhibit 5'-3' exonucleolytic cleavage. While not being bound by theory, a 5' conjugate, such as naproxen or ibuprofen, may inhibit exonucleolytic cleavage by sterically blocking the exonuclease from binding to the 5'-end of oligonucleotide. Even small alkyl chains, aryl groups, or heterocyclic conjugates or modified sugars (D-ribose, deoxyribose, glucose etc.) can block 3'-5'-exonucleases.

An iRNA agent can have increased resistance to nucleases when a duplexed iRNA agent includes a single-stranded nucleotide overhang on at least one end. In preferred embodiments, the nucleotide overhang includes 1 to 4, preferably 2 to 3, unpaired nucleotides. In a preferred embodiment, the unpaired nucleotide of the single-stranded overhang that is directly adjacent to the terminal nucleotide pair contains a purine base, and the terminal nucleotide pair is a G-C pair, or at least two of the last four complementary nucleotide pairs are G-C pairs. In further embodiments, the nucleotide overhang may have 1 or 2 unpaired nucleotides, and in an exemplary embodiment the nucleotide overhang is 5'-GC-3'. In preferred embodiments, the nucleotide overhang is on the 3'-end of the antisense strand. In one embodiment, the iRNA agent includes the motif 5'-CGC-3' on the 3'-end of the antisense strand, such that a 2-nt overhang 5'-GC-3' is formed.

Thus, an iRNA agent can include modifications so as to inhibit degradation, e.g., by nucleases, e.g., endonucleases or exonucleases, found in the body of a subject. These monomers are referred to herein as NRMs, or Nuclease Resistance promoting Monomers, the corresponding modifications as NRM modifications. In many cases these modifications will modulate other properties of the iRNA agent as well, e.g., the ability to interact with a protein, e.g., a transport protein, e.g., serum albumin, or a member of the RISC, or the ability of the first and second sequences to form a duplex with one another or to form a duplex with another sequence, e.g., a target molecule.

One or more different NRM modifications can be introduced into an iRNA agent or into a sequence of an iRNA agent. An NRM modification can be used more than once in a sequence or in an iRNA agent.

NRM modifications include some which can be placed only at the terminus and others which can go at any position. Some NRM modifications can inhibit hybridization so it is preferable to use them only in terminal regions, and preferable to not use them at the cleavage site or in the cleavage region of a sequence which targets a subject sequence or gene, particularly on the antisense strand. They can be used anywhere in a sense strand, provided that sufficient hybridization between the two strands of the ds iRNA agent is maintained. In some embodiments it is desirable to put the NRM at the cleavage site or in the cleavage region of a sense strand, as it can minimize off-target silencing.

In most cases, NRM modifications will be distributed differently depending on whether they are comprised on a sense or antisense strand. If on an antisense strand, modifications which interfere with or inhibit endonuclease cleavage should not be inserted in the region which is subject to RISC mediated cleavage, e.g., the cleavage site or the cleavage region (As described in Elbashir et al., 2001, Genes and Dev. 15: 188, hereby incorporated by reference). Cleavage of the target occurs about in the middle of a 20 or 21 nt antisense strand, or about 10 or 11 nucleotides upstream of the first nucleotide on the target mRNA which is complementary to the antisense strand. As used herein cleavage site refers to the nucleotides on either side of the cleavage site, on the target or on the iRNA agent strand which hybridizes to it. Cleavage region means the nucleotides within 1,2, or 3 nucleotides of the cleavagee site, in either direction.

Such modifications can be introduced into the terminal regions, e.g., at the terminal position or with 2, 3, 4, or 5 positions of the terminus, of a sense or antisense strand.

Tethered Ligands

The properties of an iRNA agent, including its pharmacological properties, can be influenced and tailored, for example, by the introduction of ligands, e.g. tethered ligands.

A wide variety of entities, e.g., ligands, can be tethered to an iRNA agent, e.g., to the carrier of a ligand-conjugated monomer subunit. Examples are described below in the context of a ligand-conjugated monomer subunit but that is only preferred, entities can be coupled at other points to an iRNA agent.

Preferred moieties are ligands, which are coupled, preferably covalently, either directly or indirectly via an intervening tether, to the carrier. In preferred embodiments, the ligand is attached to the carrier via an intervening tether. The ligand or tethered ligand may be present on the ligand-conjugated monomer when the ligand-conjugated monomer is incorporated into the growing strand. In some embodiments, the ligand may be incorporated into a "precursor" ligand-conjugated monomer subunit after a "precursor" ligand-conjugated monomer subunit has been incorporated into the growing strand. For example, a monomer having, e.g., an amino-terminated tether, e.g., TAP-$(CH_2)_nNH_2$ may be incorporated into a growing sense or antisense strand. In a subsequent operation, i.e., after incorporation of the precursor monomer subunit into the strand, a ligand having an electrophilic group, e.g., a pentafluorophenyl ester or aldehyde group, can subsequently be attached to the precursor ligand-conjugated monomer by coupling the electrophilic group of the ligand with the terminal nucleophilic group of the precursor ligand-conjugated monomer subunit tether.

In preferred embodiments, a ligand alters the distribution, targeting or lifetime of an iRNA agent into which it is incorporated. In preferred embodiments a ligand provides an enhanced affinity for a selected target, e.g., molecule, cell or cell type, compartment, e.g., a cellular or organ compartment, tissue, organ or region of the body, as, e.g., compared to a species absent such a ligand.

Preferred ligands can improve transport, hybridization, and specificity properties and may also improve nuclease resistance of the resultant natural or modified oligoribonucleotide, or a polymeric molecule comprising any combination of monomers described herein and/or natural or modified ribonucleotides.

Ligands in general can include therapeutic modifiers, e.g., for enhancing uptake; diagnostic compounds or reporter groups e.g., for monitoring distribution; cross-linking agents; nuclease-resistance conferring moieties; and natural or unusual nucleobases. General examples include lipophilic moleculeses, lipids, lectins, steroids (e.g., uvaol, hecigenin, diosgenin), terpenes (e.g., triterpenes, e.g., sarsasapogenin, Friedelin, epifriedelanol derivatized lithocholic acid), vitamins, carbohydrates (e.g., a dextran, pullulan, chitin, chitosan, inulin, cyclodextrin or hyaluronic acid), proteins, protein binding agents, integrin targeting molecules, polycationics, peptides, polyamines, and peptide mimics.

The ligand may be a naturally occurring or recombinant or synthetic molecule, such as a synthetic polymer, e.g., a synthetic polyamino acid. Examples of polyamino acids include polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly(2-ethylacrylic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic moieties, e.g., cationic lipid, cationic porphyrin, quaternary salt of a polyamine, or an alpha helical peptide.

Ligands can also include targeting groups, e.g., a cell or tissue targeting agent, e.g., a thyrotropin, melanotropin, surfactant protein A, Mucin carbohydrate, a glycosylated polyaminoacid, transferrin, bisphosphonate, polyglutamate, polyaspartate, or an RGD peptide or RGD peptide mimetic.

Ligands can be proteins, e.g., glycoproteins, lipoproteins, e.g. low density lipoprotein (LDL), or albumins, e.g. human serum albumin (HSA), or peptides, e.g., molecules having a specific affinity for a co-ligand, or antibodies e.g., an antibody, that binds to a specified cell type such as a cancer cell, endothelial cell, or bone cell. Ligands may also include hormones and hormone receptors. They can also include non-peptidic species, such as cofactors, multivalent lactose, multivalent galactose, N-acetyl-galactosamine, N-acetyl-glucosamine, multivalent mannose, or multivalent fucose. The ligand can be, for example, a lipopolysaccharide, an activator of p38 MAP kinase, or an activator of NF-κB.

The ligand can be a substance, e.g, a drug, which can increase the uptake of the iRNA agent into the cell, for example, by disrupting the cell's cytoskeleton, e.g., by disrupting the cell's microtubules, microfilaments, and/or intermediate filaments. The drug can be, for example, taxon, vincristine, vinblastine, cytochalasin, nocodazole, japlakinolide, latrunculin A, phalloidin, swinholide A, indanocine, or myoservin.

In one aspect, the ligand is a lipid or lipid-based molecule. Such a lipid or lipid-based molecule preferably binds a serum protein, e.g., human serum albumin (HSA). An HSA binding ligand allows for distribution of the conjugate to a target tissue, e.g., liver tissue, including parenchymal cells of the liver. Other molecules that can bind HSA can also be used as ligands. For example, neproxin or aspirin can be used. A lipid or lipid-based ligand can (a) increase resistance to degradation of the conjugate, (b) increase targeting or transport into a target cell or cell membrane, and/or (c) can be used to adjust binding to a serum protein, e.g., HSA.

A lipid based ligand can be used to modulate, e.g., control the binding of the conjugate to a target tissue. For example, a lipid or lipid-based ligand that binds to HSA more strongly will be less likely to be targeted to the kidney and therefore less likely to be cleared from the body. A lipid or lipid-based ligand that binds to HSA less strongly can be used to target the conjugate to the kidney.

In a preferred embodiment, the lipid based ligand binds HSA. Preferably, it binds HSA with a sufficient affinity such that the conjugate will be preferably distributed to a non-kidney tissue. However, it is preferred that the affinity not be so strong that the HSA-ligand binding cannot be reversed.

In another aspect, the ligand is a moiety, e.g., a vitamin or nutrient, which is taken up by a target cell, e.g., a proliferating cell. These are particularly useful for treating disorders characterized by unwanted cell proliferation, e.g., of the malignant or non-malignant type, e.g., cancer cells. Exemplary vitamins include vitamin A, E, and K. Other exemplary vitamins include the B vitamins, e.g., folic acid, B12, riboflavin, biotin, pyridoxal or other vitamins or nutrients taken up by cancer cells.

In another aspect, the ligand is a cell-permeation agent, preferably a helical cell-permeation agent. Preferably, the agent is amphipathic. An exemplary agent is a peptide such as tat or antennapedia. If the agent is a peptide, it can be modified, including a peptidylmimetic, invertomers, non-peptide or pseudo-peptide linkages, and use of D-amino acids. The helical agent is preferably an alpha-helical agent, which preferably has a lipophilic and a lipophobic phase.

5'-Phosphate Modifications

In preferred embodiments, iRNA agents are 5' phosphorylated or include a phosphoryl analog at the 5' prime terminus. 5'-phosphate modifications of the antisense strand include those which are compatible with RISC mediated gene silencing. Suitable modifications include: 5'-monophosphate ((HO)2(O)P—O-5'); 5'-diphosphate ((HO)2(O)P—O—P(HO)(O)—O-5'); 5'-triphosphate ((HO)2(O)P—O—(HO)(O)P—O—P(HO)(O)—O-5'); 5'-guanosine cap (7-methylated or non-methylated) (7m-G-O-5'-(HO)(O)P—O—(HO)(O)P—O—P(HO)(O)—O-5'); 5'-adenosine cap (Appp), and any modified or unmodified nucleotide cap structure (N—O-5'-(HO)(O)P—O—(HO)(O)P—O—P(HO)(O)—O-5'); 5'-monothiophosphate (phosphorothioate; (HO)2(S)P—O-5'); 5'-monodithiophosphate (phosphorodithioate; (HO)(HS)(S)P—O-5'), 5'-phosphorothiolate ((HO)2(O)P—S-5'); any additional combination of oxygen/sulfur replaced monophosphate, diphosphate and triphosphates (e.g. 5'-alpha-thiotriphosphate, 5'-gamma-thiotriphosphate, etc.), 5'-phosphoramidates ((HO)2(O)P—NH-5', (HO)(NH2)(O)P—O-5'), 5'-alkylphosphonates (R=alkyl=methyl, ethyl, isopropyl, propyl, etc., e.g. RP(OH)(O)—O-5'-, (OH)2(O)P-5'-CH2—), 5'-alkyletherphosphonates (R=alkylether=methoxymethyl (MeOCH2—), ethoxymethyl, etc., e.g. RP(OH)(O)—O-5'-).

The sense strand can be modified in order to inactivate the sense strand and prevent formation of an active RISC, thereby potentially reducing off-target effects. This can be accomplished by a modification which prevents 5'-phosphorylation of the sense strand, e.g., by modification with a 5'-O-methyl ribonucleotide (see Nykänen et al., (2001) ATP requirements and small interfering RNA structure in the RNA interference pathway. Cell 107, 309-321.) Other modifications which prevent phosphorylation can also be used, e.g., simply substituting the 5'-OH by H rather than O-Me. Alternatively, a large bulky group may be added to the 5'-phosphate turning it into a phosphodiester linkage.

Transport of iRNA Agents into Cells

Not wishing to be bound by any theory, the chemical similarity between cholesterol-conjugated iRNA agents and certain constituents of lipoproteins (e.g. cholesterol, cholesteryl esters, phospholipids) may lead to the association of iRNA agents with lipoproteins (e.g. LDL, HDL) in blood and/or the interaction of the iRNA agent with cellular components having an affinity for cholesterol, e.g. components of the cholesterol transport pathway. Lipoproteins as well as their constituents are taken up and processed by cells by various active and passive transport mechanisms, for example, without limitation, endocytosis of LDL-receptor bound LDL, endocytosis of oxidized or otherwise modified LDLs through interaction with Scavenger receptor A, Scavenger receptor B1-mediated uptake of HDL cholesterol in the liver, pinocytosis, or transport of cholesterol across membranes by ABC (ATP-binding cassette) transporter proteins, e.g. ABC-A1, ABC-G1 or ABC-G4. Hence, cholesterol-conjugated iRNA agents could enjoy facilitated uptake by cells possessing such transport mechanisms, e.g. cells of the liver. As such, the present invention provides evidence and general methods for targeting iRNA agents to cells expressing certain cell surface components, e.g. receptors, by conjugating a natural ligand for such component (e.g. cholesterol) to the iRNA agent, or by conjugating a chemical moiety (e.g. cholesterol) to the iRNA agent which associates with or binds to a natural ligand for the component (e.g. LDL, HDL).

Other Embodiments

An RNA, e.g., an iRNA agent, can be produced in a cell in vivo, e.g., from exogenous DNA templates that are delivered into the cell. For example, the DNA templates can be inserted into vectors and used as gene therapy vectors. Gene therapy vectors can be delivered to a subject by, for example, intravenous injection, local administration (U.S. Pat. No. 5,328,470), or by stereotactic injection (see, e.g., Chen et al., Proc. Natl. Acad. Sci. USA 91:3054-3057, 1994). The pharmaceutical preparation of the gene therapy vector can include the gene therapy vector in an acceptable diluent, or can comprise a slow release matrix in which the gene delivery vehicle is imbedded. The DNA templates, for example, can include two transcription units, one that produces a transcript that includes the top strand of an iRNA agent and one that produces a transcript that includes the bottom strand of an iRNA agent. When the templates are transcribed, the iRNA agent is produced, and processed into siRNA agent fragments that mediate gene silencing.

Formulation

The iRNA agents described herein can be formulated for administration to a subject.

For ease of exposition, the formulations, compositions, and methods in this section are discussed largely with regard to unmodified iRNA agents. It should be understood, however, that these formulations, compositions, and methods can be practiced with other iRNA agents, e.g., modified iRNA agents, and such practice is within the invention.

A formulated iRNA composition can assume a variety of states. In some examples, the composition is at least partially crystalline, uniformly crystalline, and/or anhydrous (e.g., less than 80, 50, 30, 20, or 10% water). In another example, the iRNA is in an aqueous phase, e.g., in a solution that includes water.

The aqueous phase or the crystalline compositions can, e.g., be incorporated into a delivery vehicle, e.g., a liposome (particularly for the aqueous phase) or a particle (e.g., a microparticle as can be appropriate for a crystalline composition). Generally, the iRNA composition is formulated in a manner that is compatible with the intended method of administration.

An iRNA preparation can be formulated in combination with another agent, e.g., another therapeutic agent or an agent that stabilizes a iRNA, e.g., a protein that complexes with iRNA to form an iRNP. Still other agents include chelators, e.g., EDTA (e.g., to remove divalent cations such as $Mg^{2+}$), salts, RNAse inhibitors (e.g., a broad specificity RNAse inhibitor such as RNAsin) and so forth.

In one embodiment, the iRNA preparation includes two or more iRNA agents, e.g., a second iRNA agent that can mediate RNAi with respect to a second gene, or with respect to the same gene. Still other preparations can include at least three, five, ten, twenty, fifty, or a hundred or more different iRNA species. Such iRNAs can mediated RNAi with respect to a similar number of different genes.

Where the two or more iRNA agents in such preparation target the same gene, they can have target sequences that are non-overlapping and non-adjacent, or the target sequences may be overlapping or adjacent.

Optionally, the iRNA agents of the invention may be formulated using liposomes. Liposomes of various compositions can be used for site-specific delivery of various pharmaceutically active ingredients (Witschi, C. et al., Pharm. Res., 1999, 16:382-390; Yeh, M. K. et al., Pharm. Res., 1996, 1693-1698). The interaction between the liposomes and the cargo usually relies on hydrophobic interactions or charge attractions, particularly in the case of cationic lipid delivery systems (Zelphati, O. et al., J. Biol. Chem., 2001, 276:35103-35110). HIV tat peptide-bearing liposomes have also been constructed and used to deliver cargo directly into the cytoplasm, bypassing the endocytotic pathway (Torchilin V. P. et al., Biochim. Biophys. Acta—Biomembranes, 2001, 1511:397-411; Torchilin V. P. et al., Proc. Natl. Acad. Sci. USA, 2001, 98:8786-8791). When encapsulated in sugar-grafted liposomes, pentamidine isethionate and a derivative have been found to be more potent in comparison to normal liposome-encapsulated drug or to the free drug (Banerjee, G. et al., J. Antimicrob. Chemother., 1996, 38(1): 145-150). A thermo-sensitive liposomal taxol formulation (heat-mediated targeted drug delivery) has been administered in vivo to tumor-bearing mice in combination with local hyperthermia, and a significant reduction in tumor volume and an increase in survival time was observed compared to the equivalent dose of free taxol with or without hyperthermia (Sharma, D. et al., Melanoma Res., 1998, 8(3):240-244). Topical application of liposome preparations for delivery of insulin, IFN-alpha, IFN-gamma, and prostaglandin E1 have met with some success (Cevc G. et al., Biochim. Biophys, Acta, 1998, 1368:201-215; Foldvari M. et al., J. Liposome Res., 1997, 7:115-126; Short S. M. et al., Pharm. Res., 1996, 13:1020-1027; Foldvari M. et al., Urology, 1998, 52(5):838-843; U.S. Pat. No. 5,853,755).

Antibodies represent another targeting device that may make liposome uptake tissue-specific or cell-specific (Mastrobattista, E. et al., Biochim. Biophys. Acta, 1999, 1419 (2):353-363; Mastrobattista, E. et al., Adv. Drug Deliv. Rev., 1999, 40(1-2):103-127). The liposome approach offers several advantages, including the ability to slowly release encapsulated active ingredients, the capability of evading the immune system and proteolytic enzymes, and the ability to target tumors and cause preferentially accumulation in tumor tissues and their metastases by extravasation through their leaky neovasculature. Other carriers have also been used to deliver anti-cancer drugs to neoplastic cells, such as polyvinylpyrrolidone nanoparticles and maleylated bovine serum albumin (Sharma, D. et al., Oncol. Res., 1996, 8(7-8):281-286; Mukhopadhyay, A. et al., FEBS Lett., 1995, 376(1-2):95-98). Thus, using targeting and encapsulation technologies, which are very versatile and amenable to rational design and modification, delivery of an iRNA agent of the invention to desired cells can be facilitated.

As indicated above, the pharmaceutical composition of the present invention can include a liposome component. According to the present invention, a liposome comprises a lipid composition that is capable of fusing with the plasma membrane of a cell, thereby allowing the liposome to deliver a cargo, e.g. a nucleic acid molecule composition, into a cell. Some preferred liposomes include those liposomes commonly used in gene delivery methods known to those of skill in the art. Some preferred liposome delivery vehicles comprise multilamellar vesicle (MLV) lipids and extruded lipids, although the invention is not limited to such liposomes. Methods for preparation of MLVs are well known in the art. "Extruded lipids" are also contemplated. Extruded lipids are lipids that are prepared similarly to MLV lipids, but which are subsequently extruded through filters of decreasing size, as described in Templeton et al., Nature Biotech., 1997, 15:647-652, which is incorporated herein by reference in its entirety. Small unilamellar vesicle (SUV) lipids can also be used in the compositions and methods of the present invention. Other preferred liposome delivery vehicles comprise liposomes having a polycationic lipid composition (i.e., cationic liposomes). For example, cationic liposome compositions include, but are not limited to, any cationic liposome complexed with cholesterol, and without limitation, include DOTMA and cholesterol, DOTAP and cholesterol, DOTIM and cholesterol, and DDAB and cholesterol. Liposomes utilized in the present invention can be any size, including from about 10 to 1000 nanometers (nm), or any size in between.

A liposome delivery vehicle can be modified to target a particular site in a mammal, thereby targeting and making use of an iRNA agent of the present invention at that site. Suitable modifications include manipulating the chemical formula of the lipid portion of the delivery vehicle. Manipulating the chemical formula of the lipid portion of the delivery vehicle can elicit the extracellular or intracellular targeting of the delivery vehicle. For example, a chemical can be added to the lipid formula of a liposome that alters the charge of the lipid bilayer of the liposome so that the liposome fuses with particular cells having particular charge characteristics. In one embodiment, other targeting mechanisms, such as targeting by addition of exogenous targeting molecules to a liposome (i.e., antibodies) may not be a necessary component of the liposome of the present invention, since effective immune activation at immunologically active organs can already be provided by the composition when the route of delivery is intravenous or intraperitoneal, without the aid of additional targeting mechanisms. However, in some embodiments, a liposome can be directed to a particular target cell or tissue by using a targeting agent, such as an antibody, soluble receptor or ligand, incorporated with the liposome, to target a particular cell or tissue to which the targeting molecule can bind. Targeting liposomes are described, for example, in Ho et al., Biochemistry, 1986, 25: 5500-6; Ho et al., J Biol Chem, 1987a, 262: 13979-84; Ho et al., J Biol Chem, 1987b, 262: 13973-8; and U.S. Pat. No. 4,957,735 to Huang et al., each of which is incorporated herein by reference in its entirety). In one embodiment, if avoidance of the efficient uptake of injected liposomes by reticuloendothelial system cells due to opsonization of liposomes by plasma proteins or other factors is desired, hydrophilic lipids, such as gangliosides (Allen et al., FEBS Lett, 1987, 223: 42-6) or polyethylene glycol (PEG)-derived lipids (Klibanov et al., FEBS Lett, 1990, 268: 235-7), can be incorporated into the bilayer of a conventional liposome to form the so-called sterically-stabilized or "stealth" liposomes (Woodle et al., Biochim Biophys Acta, 1992, 1113: 171-99). Variations of such liposomes are described, for example, in U.S. Pat. No. 5,705,187 to Unger et al., U.S. Pat. No. 5,820,873 to Choi et al., U.S. Pat. No. 5,817,856 to Tirosh et al.; U.S. Pat. No. 5,686,101 to Tagawa et al.; U.S. Pat. No. 5,043,164 to Huang et al., and U.S. Pat. No. 5,013,556 to Woodle et al., all of which are incorporated herein by reference in their entireties).

Treatment Methods and Routes of Delivery

A composition that includes an iRNA agent, e.g., an iRNA agent that targets MLL-AF4, can be delivered to a subject by a variety of routes. Exemplary routes include intrathecal, parenchymal, intravenous, nasal, oral, and ocular delivery. The preferred means of administering the iRNA agents of the present invention is through parenteral administration.

An iRNA agent can be incorporated into pharmaceutical compositions suitable for administration. For example, compositions can include one or more species of an iRNA agent and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The pharmaceutical compositions of the present invention may be administered in a number of ways depending upon whether local or systemic treatment is desired and upon the area to be treated. Administration may be topical (including ophthalmic, intranasal, transdermal), oral or parenteral. Parenteral administration includes intravenous drip, subcutaneous, intraperitoneal or intramuscular injection, or intrathecal or intraventricular administration.

The route of delivery can be dependent on the disorder of the patient. In general, the delivery of the iRNA agents of the present invention is done to achieve systemic delivery into the subject. The preferred means of achieving this is through parental administration.

Formulations for parenteral administration may include sterile aqueous solutions which may also contain buffers, diluents and other suitable additives. Intraventricular injection may be facilitated by an intraventricular catheter, for example, attached to a reservoir. For intravenous use, the total concentration of solutes should be controlled to render the preparation isotonic.

Administration can be provided by the subject or by another person, e.g., a another caregiver. A caregiver can be any entity involved with providing care to the human: for example, a hospital, hospice, doctor's office, outpatient clinic; a healthcare worker such as a doctor, nurse, or other practitioner; or a spouse or guardian, such as a parent. The medication can be provided in measured doses or in a dispenser which delivers a metered dose.

The term "therapeutically effective amount" is the amount present in the composition that is needed to provide the desired level of drug in the subject to be treated to give the anticipated physiological response.

The term "physiologically effective amount" is that amount delivered to a subject to give the desired palliative or curative effect.

The term "pharmaceutically acceptable carrier" means that the carrier can be taken into the lungs with no significant adverse toxicological effects on the lungs.

The term "co-administration" refers to administering to a subject two or more agents, and in particular two or more iRNA agents. The agents can be contained in a single pharmaceutical composition and be administered at the same time, or the agents can be contained in separate formulation and administered serially to a subject. So long as the two agents can be detected in the subject at the same time, the two agents are said to be co-administered.

The types of pharmaceutical excipients that are useful as carrier include stabilizers such as human serum albumin (HSA), bulking agents such as carbohydrates, amino acids and polypeptides; pH adjusters or buffers; salts such as sodium chloride; and the like. These carriers may be in a crystalline or amorphous form or may be a mixture of the two.

Bulking agents that are particularly valuable include compatible carbohydrates, polypeptides, amino acids or combinations thereof. Suitable carbohydrates include monosaccharides such as galactose, D-mannose, sorbose, and the like; disaccharides, such as lactose, trehalose, and the like; cyclodextrins, such as 2-hydroxypropyl-.beta.-cyclodextrin; and polysaccharides, such as raffinose, maltodextrins, dextrans, and the like; alditols, such as mannitol, xylitol, and the like. A preferred group of carbohydrates includes lactose, threhalose, raffinose maltodextrins, and mannitol. Suitable polypeptides include aspartame. Amino acids include alanine and glycine, with glycine being preferred.

Suitable pH adjusters or buffers include organic salts prepared from organic acids and bases, such as sodium citrate, sodium ascorbate, and the like; sodium citrate is preferred.

Dosage. An iRNA agent can be administered at a unit dose less than about 75 mg per kg of bodyweight, or less than about 70, 60, 50, 40, 30, 20, 10, 5, 2, 1, 0.5, 0.1, 0.05, 0.01, 0.005, 0.001, or 0.0005 mg per kg of bodyweight, and less than 200 mmole of RNA agent (e.g., about $4.4 \times 10^{16}$ copies) per kg of bodyweight, or less than 1500, 750, 300, 150, 75, 15, 7.5, 1.5, 0.75, 0.15, 0.075, 0.015, 0.0075, 0.0015, 0.00075, 0.00015 nmole of RNA agent per kg of bodyweight. The unit dose, for example, can be administered by injection (e.g., intravenous or intramuscular, intrathecally, or directly into an organ), an inhaled dose, or a topical application.

Delivery of an iRNA agent directly to an organ (e.g., directly to the liver) can be at a dosage on the order of about 0.00001 mg to about 3 mg per organ, or preferably about 0.0001-0.001 mg per organ, about 0.03-3.0 mg per organ, about 0.1-3.0 mg per eye or about 0.3-3.0 mg per organ.

The dosage can be an amount effective to treat or prevent a disease or disorder.

In one embodiment, the unit dose is administered less frequently than once a day, e.g., less than every 2, 4, 8 or 30 days. In another embodiment, the unit dose is not administered with a frequency (e.g., not a regular frequency). For example, the unit dose may be administered a single time. Because iRNA agent mediated silencing can persist for several days after administering the iRNA agent composition, in many instances, it is possible to administer the composition with a frequency of less than once per day, or, for some instances, only once for the entire therapeutic regimen.

In one embodiment, a subject is administered an initial dose, and one or more maintenance doses of an iRNA agent, e.g., a double-stranded iRNA agent, or siRNA agent, (e.g., a precursor, e.g., a larger iRNA agent which can be processed into an siRNA agent, or a DNA which encodes an iRNA agent, e.g., a double-stranded iRNA agent, or siRNA agent, or precursor thereof). The maintenance dose or doses are generally lower than the initial dose, e.g., one-half less of the initial dose. A maintenance regimen can include treating the subject with a dose or doses ranging from 0.01 µg to 75 mg/kg of body weight per day, e.g., 70, 60, 50, 40, 30, 20, 10, 5, 2, 1, 0.5, 0.1, 0.05, 0.01, 0.005, 0.001, or 0.0005 mg per kg of bodyweight per day. The maintenance doses are preferably administered no more than once every 5, 10, or 30 days. Further, the treatment regimen may last for a period of time which will vary depending upon the nature of the particular disease, its severity and the overall condition of the patient. In preferred embodiments the dosage may be delivered no more than once per day, e.g., no more than once per 24, 36, 48, or more hours, e.g., no more than once every 5 or 8 days. Following treatment, the patient can be monitored for changes in his condition and for alleviation of the symptoms of the disease state. The dosage of the compound may either be increased in the event the patient does not respond significantly to current dosage levels, or the dose may be decreased if an alleviation of the symptoms of the disease state is observed, if the disease state has been ablated, or if undesired side-effects are observed.

The effective dose can be administered in a single dose or in two or more doses, as desired or considered appropriate under the specific circumstances. If desired to facilitate repeated or frequent infusions, implantation of a delivery device, e.g., a pump, semi-permanent stent (e.g., intravenous, intraperitoneal, intracisternal or intracapsular), or reservoir may be advisable.

Following successful treatment, it may be desirable to have the patient undergo maintenance therapy to prevent the recurrence of the disease state, wherein the compound featured in the invention is administered in maintenance doses, ranging from 0.01 μg to 100 g per kg of body weight (see U.S. Pat. No. 6,107,094).

The concentration of the iRNA agent composition is an amount sufficient to be effective in treating or preventing a disorder or to regulate a physiological condition in humans. The concentration or amount of iRNA agent administered will depend on the parameters determined for the agent and the method of administration, e.g. nasal, buccal, or pulmonary. For example, nasal formulations tend to require much lower concentrations of some ingredients in order to avoid irritation or burning of the nasal passages. It is sometimes desirable to dilute an oral formulation up to 10-100 times in order to provide a suitable nasal formulation.

Certain factors may influence the dosage required to effectively treat a subject, including but not limited to the severity of the disease or disorder, previous treatments, the general health and/or age of the subject, and other diseases present. It will also be appreciated that the effective dosage of an iRNA agent such as an siRNA agent used for treatment may increase or decrease over the course of a particular treatment. Changes in dosage may result and become apparent from the results of diagnostic assays as described herein. For example, the subject can be monitored after administering an iRNA agent composition. Based on information from the monitoring, an additional amount of the iRNA agent composition can be administered.

Dosing is dependent on severity and responsiveness of the disease condition to be treated, with the course of treatment lasting from several days to several months, or until a cure is effected or a diminution of disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual compounds, and can generally be estimated based on EC50s found to be effective in in vitro and in vivo animal models.

The invention is further illustrated by the following examples, which should not be construed as further limiting.

EXAMPLES

Source of Reagents

Where the source of a reagent is not specifically given herein, such reagent may be obtained from any supplier of reagents for molecular biology at a quality/purity standard for application in molecular biology.

Example 1 siRNA Synthesis

Single-stranded RNAs were produced by solid phase synthesis on a scale of 1 μmole using an Expedite 8909 synthesizer (Applied Biosystems, Applera Deutschland GmbH, Darmstadt, Germany) and controlled pore glass (CPG, 500 Å, Glen Research, Sterling Va.) as solid support. RNA and RNA containing 2'-O-methyl nucleotides were generated by solid phase synthesis employing the corresponding phosphoramidites and 2'-O-methyl phosphoramidites, respectively (Proligo Biochemie GmbH, Hamburg, Germany). These building blocks were incorporated at selected sites within the sequence of the oligoribonucleotide chain using standard nucleoside phosphoramidite chemistry such as described in Current protocols in nucleic acid chemistry, Beaucage, S. L. et al. (Edrs.), John Wiley & Sons, Inc., New York, N.Y., USA. Phosphorothioate linkages were introduced by replacement of the iodine oxidizer solution with a solution of the Beaucage reagent (Chruachem Ltd, Glasgow, UK) in acetonitrile (1%). Further ancillary reagents were obtained from Mallinckrodt Baker (Griesheim, Germany).

Deprotection and purification by anion exchange HPLC of the crude oligoribonucleotides were carried out according to established procedures. Yields and concentrations were determined by UV absorption of a solution of the respective RNA at a wavelength of 260 nm using a spectral photometer (DU 640B, Beckman Coulter GmbH, Unterschleißheim, Germany). Double stranded RNA was generated by mixing an equimolar solution of complementary strands in annealing buffer (20 mM sodium phosphate, pH 6.8; 100 mM sodium chloride), heated in a water bath at 85-90° C. for 3 minutes and cooled to room temperature over a period of 3-4 hours. The purified RNA solution was stored at −20° C. until use.

Example 2 siRNA Design

In order to identify efficient MLL-AF4 siRNAs, we performed an siRNA scan of the sequence including and flanking either side of the MLL-AF4 fusion site (Domer et al., Proc Natl Acad Sci USA 90:7884-7888, 1993; Gu et al., Cell 71:701-708, 1992; Marshalek et al., Br. J. Haematology 90:308-320, 1995). To perform the scan, we synthesized 14 different siRNAs having target sites that were overlapping and moved step-wise by one nucleotide down the sequence including the MLL-AF4 fusion site. The siRNA sequences and their target sites on the fusion mRNA are shown in Table 2. The siRNA duplexes shown in Table 2 are referred to hereinbelow as siMAX, wherein X stands for the integer number in the denomination of the sense and antisense strand making up the respective duplex in Table 2. E.g., siMA5 stands for the duplex formed from MA5s and MA5as. However, siMAx stands for the duplex formed by MA3s and MAxas (Agent No. 2 in Table 1) and siMAnm for the mismatch duplex fomed by MAmms and MAmmas.

In addition, one siRNA was synthesized homologous to the fusion site variant in RS4;11 cells (herein, siMARS). Position 1 to 21 of the sense strand of siMARS correspond to Position 4338-4358 of Genbank accession no. L22179 (version no. L22179.1 GI:347376; Domer, P. H., et al.; Proc. Natl. Acad. Sci. U.S.A. 1993; 90:7884-7888).

TABLE 2

MLL-AF4 siRNA sequences[d].
fusion mRNA: ACAAAAACCAAAAGAAAAG/CAGACCUACUCCAAUGAAGc
(SEQ ID NO:42)[c]

| | | SEQ ID NO: |
|---|---|---|
| MA1s[a] | 5' - AAG/CAGACCUACUCCAAUGAA - 3' | 1 |
| MA1as[b] | 3' - UUUUC/GUCUGGAUGAGGUUACUU - 5' | 2 |
| MA2s | 5' - AAAG/CAGACCUACUCCAAUGA - 3' | 3 |
| MA2as | 3' - CUUUUC/GUCUGGAUGAGGUUACU - 5' | 4 |
| MA3s | 5' - AAAAG /CAGACCUACUCCAAUG - 3' | 5 |
| MA3as | 3' - UCUUUUC/GUCUGGAUGAGGUUAC - 5' | 6 |
| MAxas | 3' - UCUUUUC/GUCUGGAUGAGGUU - 5' | 7 |
| MAmms | 5' - AAAAG/CUGACCUUCUCCAAUG - 3' | 8 |
| MAmmas | 3' - UCUUUUC/GACUGGAAGAGGUUAC - 5' | 9 |
| MA4s | 5' - GAAAAG/CAGACCUACUCCAAU - 3' | 10 |
| MA4as | 3' - UUCUUUUC/GUCUGGAUGAGGUUA - 5' | 11 |
| MA5s | 5' - AGAAAAG/CAGACCUACUCCAA - 3' | 12 |
| MA5as | 3' - UUUCUUUUC/GUCUGGAUGAGGUU - 5' | 13 |
| MA6s | 5' - AAGAAAAG/CAGACCUACUCCA - 3' | 14 |
| MA6as | 3' - UUUUCUUUC/GUCUGGAUGAGGU - 5' | 15 |
| MA7s | 5' - AAAGAAAAG/CAGACCUACUCC - 3' | 16 |
| MA7as | 3' - GUUUUCUUUUC/GUCUGGAUGAGG - 5' | 17 |
| MA8s | 5' - AAAAGAAAAG/CAGACCUACUC - 3' | 18 |
| MA8as | 3' - GGUUUUCUUUUC/GUCUGGAUGAG - 5' | 19 |
| MA9s | 5' - CAAAAGAAAAG/CAGACCUACU - 3' | 20 |
| MA9as | 3' - UGGUUUUCUUUUC/GUCUGGAUGA - 5' | 21 |
| MA10s | 5' - CCAAAAGAAAAG/CAGACCUAC - 3' | 22 |
| MA10as | 3' - UUGGUUUUCUUUUC/GUCUGGAUG - 5' | 23 |
| MA11s | 5' - ACCAAAAGAAAAG/CAGACCUA - 3' | 24 |
| MA11as | 3' - UUUGGUUUUCUUUUC/GUCUGGAU - 5' | 25 |
| MA12s | 5' - AACCAAAAGAAAAG/CAGACCU - 3' | 26 |
| MA12as | 3' - UUUUGGUUUUCUUUUC/GUCUGGA - 5' | 27 |
| MA13s | 5' - AAACCAAAAGAAAAG/CAGACC - 3' | 28 |
| MA13as | 3' - UUUUUGGUUUUCUUUUC/GUCUGG - 5' | 29 |
| MA14s | 5' - AAAACCAAAAGAAAAG/CAGAC - 3' | 30 |
| MA14as | 3' - GUUUUUGGUUUUCUUUUC/GUCUG - 5' | 31 |
| siMARSs | 5' - ACUUUAAGCAGACCUACUCCA - 3' | 32 |
| siMARSas | 3' - CCUGAAAUUCGUCUGGAUGAGGU - 5' | 33 |
| siAGF1s | 5' - CCUCGAAAUCGUACUGAGAAG - 3' | 34 |
| siAGF1as | 3' - UUGGAGCUUUAGCAUGACUCU - 5' | 35 |
| siAGF6s | 5' - CCUCGAAUUCGUUCUGAGAAG - 3' | 36 |
| siAGF6as | 3' - UUGGAGCUUAAGCAAGACUCU - 5' | 37 |
| siGL2s | 5' - CGUACGCGGAAUACUUCGATT - 3' | 38 |
| siGL2as | 3' - TTGCAUGCGCCUUAUGAAGCU - 5' | 39 |
| siK4s | 5' - GAUGAGGAUCGUUUCGCAUGA - 3' | 40 |
| siK4as | 3' - UCCUACUCCUAGCAAAGCGUACU - 5' | 41 |

[a]"s" indicates sense strand; [b]"as" indicates antisense strand; [c]"/" indicates the fusion site between chromosome 11 and chromosone 4 sequence; [d]duplexed siRNA agents are referenced in the specification as "siMAn", n = 1 to 14, siMAx for the duplex of MA3s with MAxas, and siMAmm for the duplex MAmms + MAmmas As controls, the mismatch siRNA siMAmm, the siRNAs siAGF1 and its mismatch control siAF6, targeting AML/MTG8, as well as siRNAs siK4 and siGL2, targeting neomycin phosphotransferase mRNA (Heidenreich et al., Blood 101:3157-3163, 2003) were used. Positions 1 to 21 in the sense strand of siAGF 1 correspond to positions 2102-2122 of AML1/MTG8, Genbank accession no. D13979. siAGF6 is identical to siAGF1 except for A→U switches in positions 8 and 13 of the sense strand sequence, and the corresponding changes to the antisense sequence. Positions 1 to 21 in the sense strand of siGL2 correspond to positions 514-533 of P. pyralis luciferase, Genbank accession no. Ml 5077. Positions 1 to 21 in the sense strand of siK4 correspond to positions 4184-4202 of Neomycin phosphotransferase II, Genbank accession No. LI1017.

The siRNAs, except siMAx, siAGF1, siAGF6, and siGL2 consisted of 21 nucleotide-long sense and 23 nucleotide-long antisense strands, and the siRNAs formed a single 3'-overhang of 2 nucleotides by the antisense strand. siMAx, siAGF1, siAGF6, and siGL2 consisted of 21 nucleotide-long sense and antisense strands, forming 3'-overhangs of 2 nucleotides on both ends.

Example 3

Cell Culture

The efficiencies of the different siRNAs to reduce the level of mRNA expressed from the several genes studied was examined in cell lines SEM (Greil et al., Br J Haematol. 86:275-283, 1994), RS4;11 (Stong, R. C., et al.; Blood 1985, 65:21-31) (obtained from the DSMZ, Braunschweig, Germany) and MV4;11 (Lange; P. H., and Winfield, H. N.; Cancer 1987; 60:464-472) (obtained from J. Krauter, Medical School Hannover, Germany) which carry the chromosomal translocation t(4;11)(q21;q23), but express different MLL-AF4 variants due to different break points. Further leukaemic cell lines used in this study were HL60 (Collins, S. J., et al.; Nature 1977; 270:347-349), K562 (Lozzio, C. B., and Lozzio, B. B.; J Natl Cancer Inst 1973; 50:535-538.), Kasumi-1 (Asou, H., et al.; Blood 1991; 77:2031-2036), SKNO-1 (Matozaki, S., et al.; Br J Haematol 1995; 89:805-811) and U937 (Sundstrom, C., and Nilsson, K.; Int J Cancer 1976; 17:565-577.). SKNO-1 cells were maintained in RPMI 1640 Glutamax medium (Invitrogen, Karlsruhe, Germany) supplemented with 20% FCS (SeraPlus, PAN Biotech GmbH) and 7 ng/ml GM-CSF, all other lines in RPMI 1640 Glutamax medium supplemented with 10% FCS at 37° C. and 5% CO2. Primary human CD34+ cells from bone marrow of healthy patients were obtained as frozen stocks from University Children's Hospital in Tübingen.

Example 4 siRNA Treatment

SiRNA electroporations of SEM were carried out as described previously (Dunne et al., Oligonucleotides, 13:375-80, 2003; and Heidenreich, et al., Blood 101:3157-3163, 2003). Electroporation was performed with a Fischer electroporator (Fischer, Heidelberg, Germany) using a rectangle pulse of 350 V for 10 ms. After incubation for 15 minutes at room temperature, the cells were diluted twenty fold with culture medium and incubated at 37° C. and 5% $CO_2$.

Example 5

RT-PCR

Levels of endogenous MLL-AF4, MLL, AF4, HOXA7, HOXA9, OAS 1 and STAT1 were assayed by Real-Time PCR. Total RNA extraction was performed with the Rneasy kit (Qiagen, Hilden, Germany) as suggested by the manufacturer. One mg of total RNA was subsequently used for the real-time reverse transcription coupled to polymerase chain reaction (RT-PCR). Reverse transcription reactions were performed using 25 mM random hexamers, 5×RT buffer, 1 mM dNTP Mix, 20 U RNase inhibitor (MBI) and 100 U MMLV-RT, RNase H-(Promega, Heidelberg, Germany). The mixture was incubated at room temperature for 10 min, for 45 min at 42° C., and 3 min at 99° C. mRNA levels of the respective genes were normalized to GAPDH mRNA levels.

Real-time PCR reaction was performed using primers for MLL-AF4, MLL, AF4, HOXA7, HOXA9, OAS1 and STAT1. Primers hybridizing to GAPDH were used as a control. The master mix (MLL-AF4) for the TaqMan real-time PCR reaction contained 62.5 nM of forward and reverse primers, 62.5% (v/v) Sybr-Green Mix. The master mix for the GAPDH reaction contained 375 nM forward and reverse primers and 62.5% (v/v) Sybr-Green-Mix. Otherwise, RT-PCR was performed as described in Martinez et al., BMC Cancer 2004, 4:44. The sequences of the primers used are listed in Table 3.

TABLE 3

PCR primer sequences

| Gene | Sense/antisense primer | SEQ ID NO: |
|---|---|---|
| MLL-AF4 | 5'-ACAGAAAAAAGTGGCTCCCCG-3'/<br>5'-TATTGCTGTCAAAGGAGGCGG-3' | 43<br>44 |
| MLL: | 5'-ACAGAAAAAAGTGGCTCCCCG-3'/<br>5'-GCAAACCACCCTGGGTGTTA-3' | 45<br>46 |
| AF4: | 5'-CAGAAGCCCACGGCTTATGT-3'/<br>5'-TATTGCTGTCAAAGGAGGCGG-3' | 47<br>48 |
| HOXA7: | 5'-CGCCAGACCTACACGCG-3'/<br>5'-CAGGTAGCGGTTGAAGTGGAA-3' | 49<br>50 |
| HOXA9: | 5'-CCACCATCCCCGCACA-3'/<br>5'-AACAGGGTTTGCCTTGGAAA-3' | 51<br>52 |
| OAS1: | 5'-TCCAAGGTGGTAAAGGGTGG-3'/<br>5'-AGGTCAGCGTCAGATCGGC-3' | 53<br>54 |
| GAPDH: | 5'-GAAGGTGAAGGTCGGAGTC-3'/<br>5'-GAAGATGGTGATGGGATTTC-3' | 55<br>56 |
| STAT1: | 5'-CATCACATTCACATGGGTGGA-3'/<br>5'-GGTTCAACCGCATGGAAGTC-3' | 57<br>58 |

Primers were designed with PRIMER-EXPRESS software (Applied Biosystems, Foster City, Calif., USA).

Example 6

Colony Formation Assay

Twenty-four hours after cell electroporation with siRNAs, 10,000 cells were plated in 0.5 ml of RPMI 1640 medium containing 20% FCS and 0.56% methylcellulose, in 24-well plates. In the case of RS4;11, cell numbers were increased to 20,000 per well. Colonies containing more than 20 cells were counted 14 days after plating. Under these conditions, mock-transfected cells (electroporated without siRNAs) yielded 50 to 100 colonies per well dependent on the cell line examined. Human Colony-Forming Cell Assays were performed using MethoCult☐ Methylcellulose-based media (CellSystems, St. Katharinen, Germany). After electroporation, 5000 human primary CD34+ cells were plated in duplicate in 35-mm culture dishes with 1 ml of methylcellulose medium. The number of CFU-GEMMs and CFU-GMs was counted 10 days after the plating.

Example 7

MTT Test

Cells were electroporated twice within 48 h and were plated on 96-well plates at the density of $0.5 \times 10^5$ cells in 100 µl/well. Every 24 h later, 10 µl of MTT solution (Roche, Mannheim, Germany) was added. After incubation for 4 hours at 37° C., cells were lysed with the solubilization solution according to the manufacturer's instruction. The OD measurements were performed using ELISA Reader (Dynex, Frankfurt/M, Germany) at 560 nm, and 650 nm as a reference wavelength. Cell numbers were calculated by cell dilution series. Human Colony-Forming Cell Assays were performed using MethoCult® Methylcellulose-based media (CellSystems, St. Katharinen, Germany). The human primary cells were electroporated and 5000 cells were subsequently plated in 35-mm culture dishes with 1 ml of methylcellulose medium. Each sample was plated in duplicate and the number of CFU-GEMMs and CFU-GMs was counted 10 days after the plating.

Example 8

Cell Cycle Analysis and Apoptosis Assay

Cell cycle analysis was performed as described previously (32). The obtained data were subsequently analyzed and evaluated using ModFit program (Verity, Topsham, USA). Apoptosis was examined with human Annexin V/FITC Kit (Bender MedSystems, Wien, Austria) according to the provider's instructions. Briefly, $2-5 \times 10^5$ cells were washed with PBS at the indicated time points after electroporation followed by incubation in the presence of Annexin-V-FITC solution for 10 min at room temperature. The cells were washed again with PBS and stained with propidium iodide. The samples were then immediately analyzed by flow cytometry using a FACSCalibur (Becton Dickinson, Heidelberg, Germany).

Example 9

Western Blotting

To obtain total cellular protein, proteins present in the flow-through of RNeasy columns were precipitated with two volumes of acetone and dissolved in urea buffer (9 M urea, 4% (w/w) 3-[(3-Cholamidopropyl)-dimethylammonio]-propansulfonat (CHAPS), 1% (w/w) Dithiothreitol). Total lysates (50 µg for MLL-AF4 detection, 10 µg for all other immunoblots) were analyzed as described (32). The following antibodies were used for immunoblot detection: Cleaved caspase-3 (Asp175) (1:1000, Cell Signaling Technology, #9661); Tubulin Ab-4 (1 mg/l, NeoMarkers MS-719-PO, Fremont, USA) Bcl-XL (1:500, BD PharMingen, #556499); MLLT2 (1:600, Orbigen, #10852); GAPDH (1:20,000, HyTest, #5G4).

Example 10

Xenotransplantation of SCID Mice

Female 4-5 week old CB-171I/lcrCrj-SCID/SCID mice were obtained from Charles River Germany. SEM cells ($2 \times 10^7$) were electroporated on day one and day 3 either without (Mock) or with 500 nM of the indicated siRNA. On day 4, cells were intraperitoneally injected into mice. Animals were maintained and treated according to protocols approved by the Regional Board Tübingen.

Example 11

Histology

Organs were removed and fixed in neutrally buffered 4% formalin at room temperature for 4-5 days followed by dehydration, embedding into paraffin and sectioning. The tissues were stained with hematoxylin (Meyer's hemalum solution, Merck, Darmstadt, Germany) and eosin (Eosin Y, Merck, Darmstadt, Germany) for light microscopy. Light microscopy was performed with a Zeiss Axioplan microscope (Zeiss, Guttingen, Germany) using a 20× Plan-Neofluar or 40× Plan-Neofluar 1.3 oil lens. Images were captured using Axio Vision 4 Software provided with the microscope and Adobe Photoshop (Adobe Systems, San Jose, Calif., USA).

Example 12

Statistical Analyses

Colony formation assays were analyzed by unpaired student's t-test. Survival curves were analyzed by log-rank test.

Example 13

Identification of siRNAs with Activity Towards Inhibition of MLL-AF4 Expression

Figure 1B:
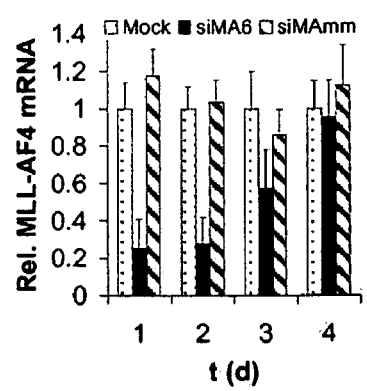
Figure 1C:
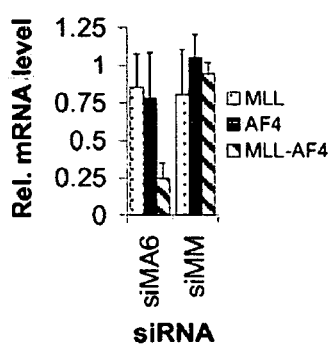
Figure 1D:
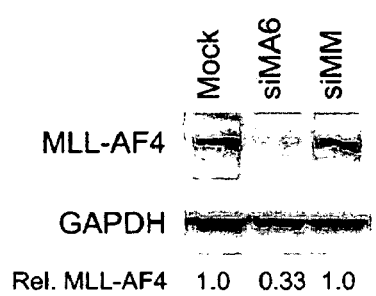
Figure 1E:
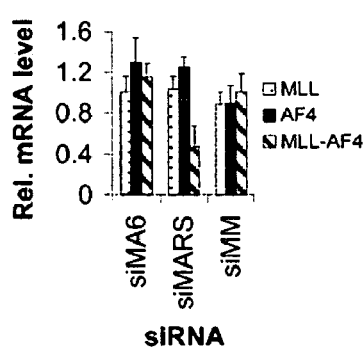

To identify highly efficient MLL-AF4 siRNAs, we performed an siRNA scan of the MLL-AF4 fusion site. For that, we synthesized 14 different siRNAs with target sites moved by one single nucleotide each. The efficiencies of the different siRNAs were examined in the t(4;11)-positive leukemic cell line SEM established from a 5 year old ALL patient in relapse (Greil, J., et al.; Br J Haematol 1994; 86:275-283). Of all 14 siRNAs examined, two siRNAs, siMA3 and siMA6, diminished MLL-AF4 mRNA levels by more than 60% (FIG. 1A). The reduction of MLL-AF4 transcript levels was dose-dependent and reached its maximum of 70% with 750 nM siRNA (data not shown). Time course experiments showed that MLL-AF4 mRNA amounts reached their minimum between 24 to 48 hours after siRNA transfection and recovered to normal levels at day 4 (FIG. 1B). Moreover, siMA6 affected neither wildtype AF4 nor MLL mRNA levels (FIG. 1C), whereas siMA3 substantially reduced AF4 levels (data not shown). The mismatch control siRNA siMM affected neither MLL-AF4 nor the corresponding wildtype allele transcripts. The decrease in MLL-AF4 mRNA levels was reflected by a concomitant 67% decrease in MLL-AF4 protein (FIG. 1D).

The MLL-AF4 fusion site varies between different t(4;11) positive cell lines. Whereas SEM cells express a transcript containing an MLL exon 9 AF4 exon 4 (e9-e4) fusion, RS4;11 express an exon 10-exon 4 (e10-e4) variant. Inspite of a homology of 67%, siMA6 did not diminish levels of the e10-e4 isoform in RS4;11 cells (Domer, P. H., et al.; Proc Natl Acad Sci U S A 1993; 90:7884-7888), whereas a perfectly homologous siRNA, siMARS, reduced MLL-AF4 e10-e4 in RS4;11 by 60%, without affecting AF4 or MLL expression.

Figure 1F:
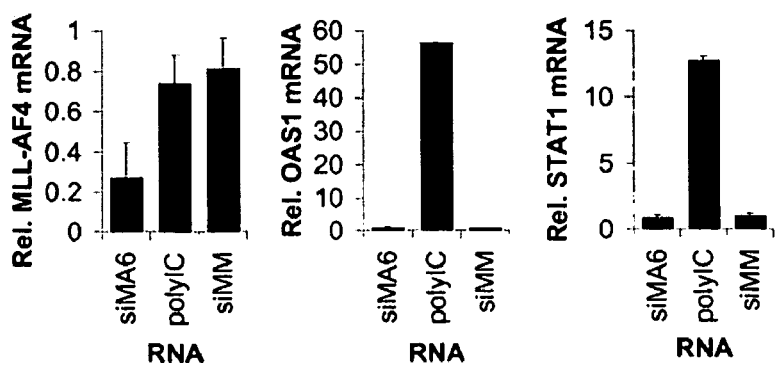

Neither siMA6 nor siMM induced STAT1 or 2'-5'-oligoadenylate synthase 1 expression (FIG. 1F) indicating that these siRNAs did not trigger an interferon response (Sledz, C. A., et al.; Nat Cell Biol 2003; 5:834-839). Transfection with polyIC increased OAS1 transcript levels more than fiftyfold and STAT1 mRNA levels more than tenfold (FIG. 1F) demonstrating the inducibility of interferon response pathways in these leukemic cells. Because of their high specificity, the MLL-AF4 siRNA siMA6 and the mismatch control siRNA siMM were chosen to proof the significance of MLL-AF4 expression for the leukemic phenotype.

Example 14

MLL-AF4 Affects Leukemic Clonogenicity

To study the relevance of MLL-AF4 for leukemic clonogenicity, we transfected t(4;11)-positive SEM cells with siRNAs followed by incubation in semisolid medium. SiMA6-mediated depletion of MLL-AF4 reduced the number of colonies fivefold (FIG. 2A). This effect was specific, since colony formation of the t(8;21)-positive leukemic cell line Kasumi-1 was not affected by siMA6. Vice versa, transfection with the AML1/MTG8-specific siRNA siAGF1 compromized Kasumi-1 colony formation without interfering with SEM colony formation (Martinez, N., et al.; BMC Cancer 2004; 4:44). None of the mismatch controls (siMM and siAGF6) affected leukemic clonogenicity. Furthermore, neither of the t(4;11)-negative leukemic cell lines HL60, K562, SKNO-1 and U937 nor the t(4;11)-positive cell lines RS4;11 and MV4;11 expressing MLL-AF4 variants not affected by siMA6 showed impaired colony formation upon siRNA transfection (data not shown). Notably, siMARS-mediated suppression of the MLL-AF4 e10-e4 variant reduced RS4;11 colony formation twofold, demonstrating the dependence of clonogenic efficacy on MLL-AF4 for another t(4;11) cell line (FIG. 2B). MLL-AF4 siRNA electroporation of primary human hemopoetic CD34+ cells did neither affect the numbers of GEMM nor GM colonies (FIG. 2C). This lack of effect cannot be attributed to inefficient siRNA transfections, since both the cell lines used here and the human hemopoetic CD34+ cells the can be efficiently transfected with functional siRNAs (Scherr, M., et al.; Blood 2003; 101:1566-1569; Heidenreich, O., et al.; Blood 2003; 101:3157-3163; Dunne, J., et al.; Oligonucleotides 2003; 13:375-380.).

Example 15

Suppression of MLL-AF4 Inhibits Leukemic Proliferation and Cell Cycle Progression Next, we examined the role of MLL-AF4 in the control of leukemic proliferation in suspension culture. Whereas a single electroporation with siMA6 did not affect the doubling time of t(4;11)-positive SEM cells (data not shown), repeating siRNA electroporations for every second day resulted in a sustained inhibition of proliferation of SEM cells by siMA6, and of RS4;11 cells by siMARS (FIG. 2D). Thus, proliferation was only inhibited by the siRNA homologous to the corresponding MLL-AF4 fusion site demonstrating the specificity of these MLL-AF4 siRNAs. Mock or siRNA-electroporated SEM or RS4;11 cells proliferated with a doubling time of 1.4 days demonstrating that the repeated electroporation did not seriously affect their proliferation.

The reduced proliferation of t(4;11)-positive cells upon MLL-AF4 depletion was paralleled by changes in the cell cycle distribution. During a time course of 10 days with repetitive MLL-AF4 siRNA electroporations, the fraction of S phase cells decreased in both SEM and RS4;11 cells from 50% to 30% and 20%, respectively, with a concomitant increase in the fraction of G0/G1 phase cells (FIG. 2E). Notably, siMA6 affected cell cycle distribution only in SEM cells, whereas siMARS caused those changes only in RS4;11 cells. Thus, depletion of MLL-AF4 negatively interferes with the progression of t(4;11)-positive cells from G1 to S phase. The impaired G1/S transition is not associated with cellular senescence, as senescence-associated β-galactosidase activity did not increase upon MLL-AF4 depletion (data not shown).

Example 16

MLL-AF4 Depletion Induces Apoptosis in t(4;11)-Positive SEM Cells

Figure 3A:
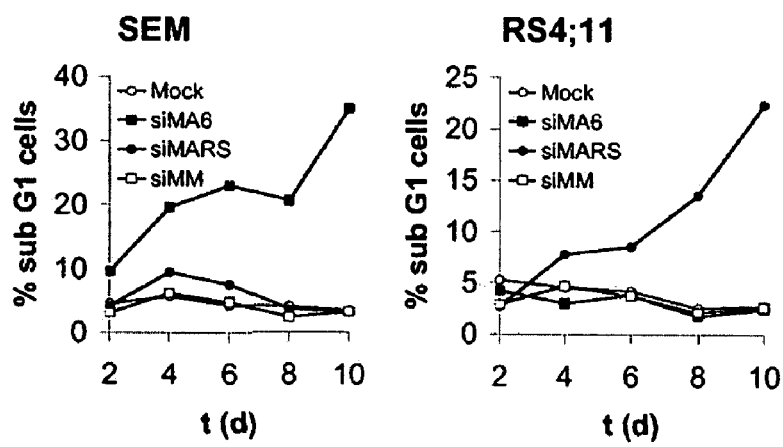
FIGS. 3A-3C. MLL-AF4 depletion induces apoptosis in t(4;11)-positive SEM and RS4;11 cells.
Figure 3B:
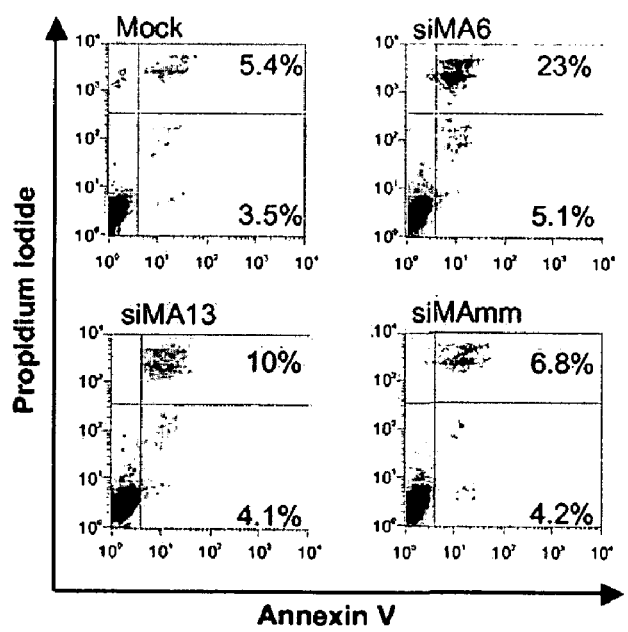
Figure 3C:
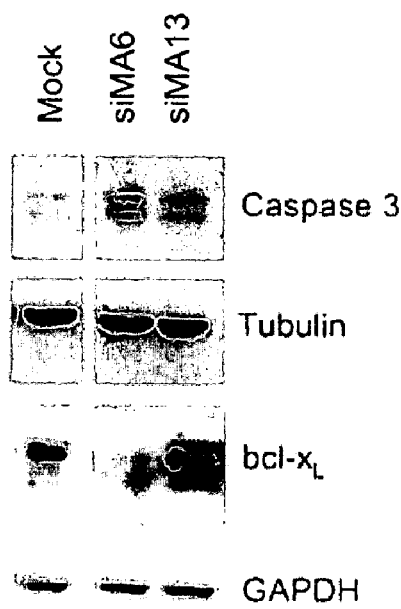

Cell cycle analysis of SEM and RS4;11 cells revealed that the continous depletion of MLL-AF4 for ten days raised the number of subG1 cells tenfold compared to controls, indicating an increased amount of apoptotic cells (FIG. 3A). Staining with annexin V and propidium iodide also demonstrated for SEM cells a threefold increase in apoptotic cells upon suppression of MLL-AF4 for four days thereby agreeing with the increase in sub G1 cells seen at the same time point (FIG. 3B). Notably, the almost inactive siRNA siMA13 (see FIG. 1A) only marginally affected the amount of apoptotic cells suggesting a direct correlation between the extent of MLL-AF depletion and the rate of apoptosis. This result was corroborated by the proteolytic activation of caspase-3 and decreased amounts of the anti-apoptotic protein Bcl-XL upon transfection with siMA6 (FIG. 3C).

Example 17

MLL-AF4 Suppression Decreases Expression of Hox Genes

Figure 4:
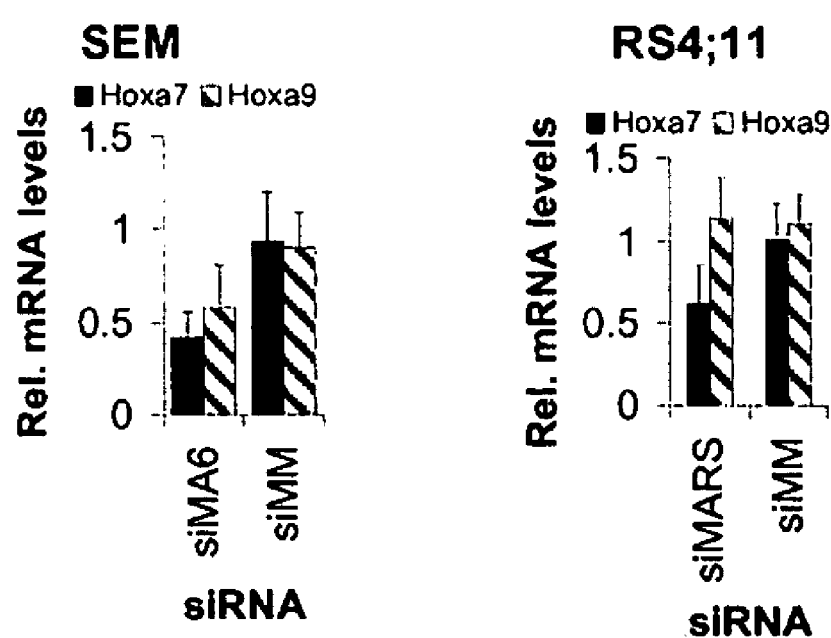
FIG. 4. MLL-AF4 suppression affects Hoxa7 and Hoxa9 gene expression. Total RNA was isolated 48 h after the second electroporation with 500 nM of the indicated siRNA and analyzed by real time RT-PCR. Error bars show standard deviations.

Since expression of MLL oncoproteins including MLL-AF4 is associated with increased expression of several Hox genes including Hoxa7 and Hoxa9 as well as of another homeotic gene, Meis1. Therefore, we analyzed the expression of these three genes in dependence on the MLL-AF4 level. After two consecutive transfections of SEM cells with the MLL-AF4 siRNA siMA6, Hoxa7 mRNA levels decreased twofold (FIG. 4). A minor reduction of Hoxa9 was also observed. In RS4;11 cells, Hoxa7, but not Hoxa9 was reduced upon transfection with siMARS. The absence of Hoxa9 reduction in RS4;11 cells might be due to the lower efficiency of the MLL-AF4 suppression compared to that in SEM cells (FIG. 1D, E).

Example 18

MLL-AF4 is Important for the Leukemic Engraftment of t(4;11)-Positive Cells

Figure 5:
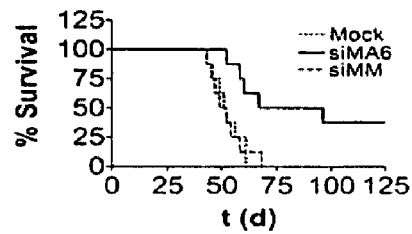
FIGS. 5A-5E. MLL-AF4 suppression diminishes leukemic engraftment.
Figure 5:
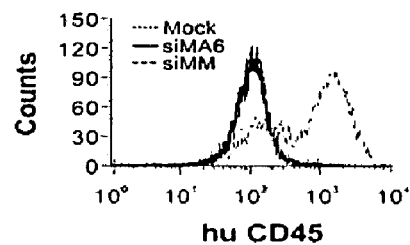
Figure 5:
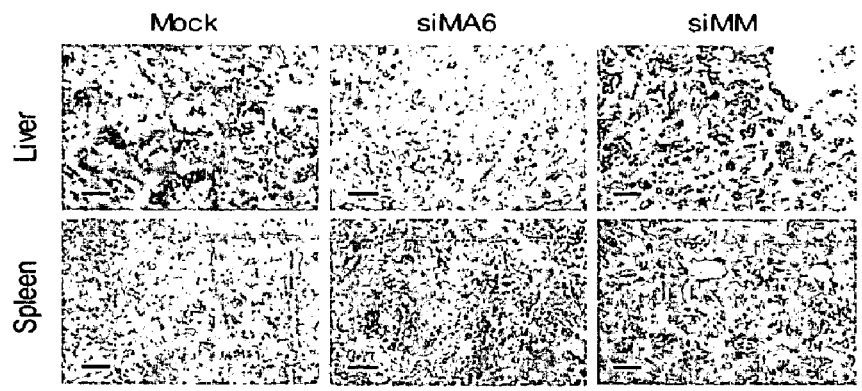
Figure 5:
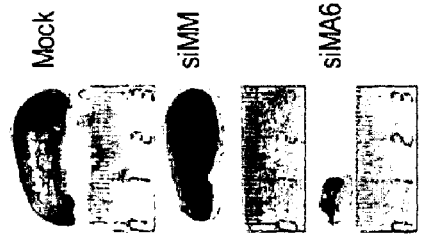
Figure 5:
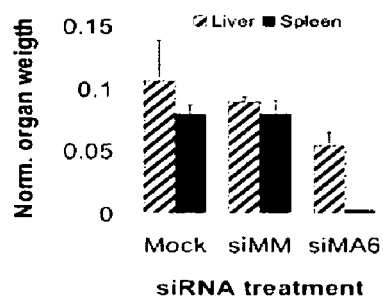

Leukemic cell growth in SCID mice has been shown to be associated with high-risk B-ALL (Uckun, F. M., et al.; Blood 1995; 85:873-878). Therefore, we used an t(4;11)—SCID mouse model to ask, whether siRNA-mediated depletion of MLL-AF4 affects engraftment and the development of leukemic disease in vivo (Pocock, C. F., et al.; Br J Haematol 1995; 90:855-867). Intraperitoneal transplantation of either mock- or control siRNA-treated SEM cells into SCID mice resulted in a 100% leukemia-associated mortality within 70 days post transplantation with a median survival of 52 and 52 days, respectively (FIG. 5A). Xenotransplantation of MLL-AF4-depleted SEM cells caused a significantly less severe phenotype with a median survival of 82 days and an overall survival of 38% at day 125 (p<0.01). Animals succumbing the disease showed ovarian tumors, splenomegaly and massive leukemic blast infiltration in bone marrow, spleen and liver, whereas the organs of a surviving animal of the siMA6 group showed no signs of leukemic infiltration 228 days after transplantation (FIG. 5B, C). In conclusion, siRNA-mediated suppression of MLL-AF4 reduced the leukemic engraftment of t(4;11)-positive cells in xenotransplanted SCID mice.

Example 19

Conclusions

Inhibition of MLL-AF expression diminished leukemic proliferation in suspension culture as well as colony formation of t(4;11) cell lines. This reduced clonogenicity and proliferation was accompanied by an increase in apoptosis. Furthermore, depletion of MLL-AF4 was accompanied by a decrease in Hoxa7, Hoxa9 and Meis-1 expression, which in turn may contribute to apoptosis. Finally, siRNA-mediated MLL-AF4 suppression seriously compromised the leukemic engraftment in xenotransplantated SCID mice. Since efficient engraftment in SCID mice predicts an increased probability of relapse in ALL patients (Uckun, F. M., et al.; Blood 1995; 85:873-878), these data suggest that interfering with MLL-AF4 functions may improve patients outcome.

Because of its exclusive expression in t(4;11) leukemic cells, and because of its central role in the maintenance of leukemia, MLL-AF4 is a very promising target for the treatment of this highly aggressive leukemia. However, currently no small molecule inhibitors specific for this fusion protein are available. We show that siRNAs homologous to the fusion site efficiently suppress MLL-AF4. Moreover, we demonstrate that two different variants of this fusion gene can be targeted with high efficacy and exclusive specificity. This exclusive specificity also proves that the observed antileukemic properties of these siRNAs are directly due to MLL-AF4 suppression and not to off-target effects, such as unintended inhibition of other genes, or induction of interferon response. Our results suggest that MLL-AF4 siRNAs may provide a specific, but still flexible and, thus, promising therapeutic tool for the treatment of t(4;11) ALL

OTHER EMBODIMENTS

A number of embodiments of the invention have been described. Nevertheless, it will be understood that various modifications may be made without departing from the spirit and scope of the invention.

What is claimed is:

1. A double stranded iRNA agent, wherein the sense strand consists of SEQ ID NO:14, and wherein the antisense strand consists of SEQ ID NO:15.

2. The iRNA agent of claim 1, further comprising a modification that causes the iRNA agent to have increased stability in a biological sample.

3. The iRNA agent of claim 1, further comprising a phosphorothioate or a 2'-modified nucleotide.

4. The iRNA agent of claim 3, wherein the 2'-modification is chosen from the group of: 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), and 2'-O-N-methylacetamido (2'-O-NMA).

5. The iRNA agent of claim 1, further comprising at least one 5'-uridine-adenine-3' (5'-UA-3') dinucleotide wherein the uridine is a 2'-modified nucleotide; at least one 5'-uridine-guanine-3'(5'-UG-3') dinucleotide, wherein the 5'-uridine is a 2'-modified nucleotide; at least one 5'-cytidine-adenine-3' (5'-CA-3') dinucleotide, wherein the 5'-cytidine is a 2'-modifiednucleotide; or at least one 5'-uridine-uridine-3' (5'-UU-3') dinucleotide, wherein the 5'-uridine is a 2'-modified nucleotide.

6. The iRNA agent of claim 1, further comprising a cholesterol moiety.

7. The iRNA agent of claim 6, wherein the cholesterol moiety is conjugated to the 3'-end of the sense strand of the iRNA agent.

\* \* \* \* \*

SEQUENCE LISTING

<160> NUMBER OF SEQ ID NOS: 58

<210> SEQ ID NO 1
<211> LENGTH: 21
<212> TYPE: RNA
<213> ORGANISM: Artificial Sequence
<220> FEATURE:
<223> OTHER INFORMATION: Synthetically generated siRNA sequence

<400> SEQUENCE: 1
aagcagaccu acuccaauga a                                            21

<210> SEQ ID NO 2
<211> LENGTH: 23
<212> TYPE: RNA
<213> ORGANISM: Artificial Sequence
<220> FEATURE:
<223> OTHER INFORMATION: Synthetically generated siRNA sequence

<400> SEQUENCE: 2
uucauuggag uaggucugcu uuu                                          23

<210> SEQ ID NO 3
<211> LENGTH: 21
<212> TYPE: RNA
<213> ORGANISM: Artificial Sequence
<220> FEATURE:
<223> OTHER INFORMATION: Synthetically generated siRNA sequence

<400> SEQUENCE: 3
aaagcagacc uacuccaaug a                                            21

```
<210> SEQ ID NO 4
<211> LENGTH: 23
<212> TYPE: RNA
<213> ORGANISM: Artificial Sequence
<220> FEATURE:
<223> OTHER INFORMATION: Synthetically generated siRNA sequence

<400> SEQUENCE: 4
ucauuggagu aggucugcuu uuc                                              23

<210> SEQ ID NO 5
<211> LENGTH: 21
<212> TYPE: RNA
<213> ORGANISM: Artificial Sequence
<220> FEATURE:
<223> OTHER INFORMATION: Synthetically generated siRNA sequence

<400> SEQUENCE: 5
aaaagcagac cuacuccaau g                                                21

<210> SEQ ID NO 6
<211> LENGTH: 23
<212> TYPE: RNA
<213> ORGANISM: Artificial Sequence
<220> FEATURE:
<223> OTHER INFORMATION: Synthetically generated siRNA sequence

<400> SEQUENCE: 6
cauuggagua ggucugcuuu ucu                                              23

<210> SEQ ID NO 7
<211> LENGTH: 21
<212> TYPE: RNA
<213> ORGANISM: Artificial Sequence
<220> FEATURE:
<223> OTHER INFORMATION: Synthetically generated siRNA sequence

<400> SEQUENCE: 7
uuggaguagg ucugcuuuuc u                                                21

<210> SEQ ID NO 8
<211> LENGTH: 21
<212> TYPE: RNA
<213> ORGANISM: Artificial Sequence
<220> FEATURE:
<223> OTHER INFORMATION: Synthetically generated siRNA sequence

<400> SEQUENCE: 8
aaaagcugac cuucuccaau g                                                21

<210> SEQ ID NO 9
<211> LENGTH: 23
<212> TYPE: RNA
<213> ORGANISM: Artificial Sequence
<220> FEATURE:
<223> OTHER INFORMATION: Synthetically generated siRNA sequence

<400> SEQUENCE: 9
cauuggagaa ggucagcuuu ucu                                              23

<210> SEQ ID NO 10
<211> LENGTH: 21
<212> TYPE: RNA
<213> ORGANISM: Artificial Sequence
<220> FEATURE:
<223> OTHER INFORMATION: Synthetically generated siRNA sequence
```

```
<400> SEQUENCE: 10
gaaaagcaga ccuacuccaa u                                            21

<210> SEQ ID NO 11
<211> LENGTH: 23
<212> TYPE: RNA
<213> ORGANISM: Artificial Sequence
<220> FEATURE:
<223> OTHER INFORMATION: Synthetically generated siRNA sequence

<400> SEQUENCE: 11
auuggaguag gucugcuuuu cuu                                          23

<210> SEQ ID NO 12
<211> LENGTH: 21
<212> TYPE: RNA
<213> ORGANISM: Artificial Sequence
<220> FEATURE:
<223> OTHER INFORMATION: Synthetically generated siRNA sequence

<400> SEQUENCE: 12
agaaaagcag accuacucca a                                            21

<210> SEQ ID NO 13
<211> LENGTH: 23
<212> TYPE: RNA
<213> ORGANISM: Artificial Sequence
<220> FEATURE:
<223> OTHER INFORMATION: Synthetically generated siRNA sequence

<400> SEQUENCE: 13
uuggaguagg ucugcuuuuc uuu                                          23

<210> SEQ ID NO 14
<211> LENGTH: 21
<212> TYPE: RNA
<213> ORGANISM: Artificial Sequence
<220> FEATURE:
<223> OTHER INFORMATION: Synthetically generated siRNA sequence

<400> SEQUENCE: 14
aagaaaagca gaccuacucc a                                            21

<210> SEQ ID NO 15
<211> LENGTH: 23
<212> TYPE: RNA
<213> ORGANISM: Artificial Sequence
<220> FEATURE:
<223> OTHER INFORMATION: Synthetically generated siRNA sequence

<400> SEQUENCE: 15
uggaguaggu cugcuuuucu uuu                                          23

<210> SEQ ID NO 16
<211> LENGTH: 21
<212> TYPE: RNA
<213> ORGANISM: Artificial Sequence
<220> FEATURE:
<223> OTHER INFORMATION: Synthetically generated siRNA sequence

<400> SEQUENCE: 16
aaagaaaagc agaccuacuc c                                            21

<210> SEQ ID NO 17
<211> LENGTH: 23
```

```
<212> TYPE: RNA
<213> ORGANISM: Artificial Sequence
<220> FEATURE:
<223> OTHER INFORMATION: Synthetically generated siRNA sequence

<400> SEQUENCE: 17
ggaguagguc ugcuuuucuu uug                                              23

<210> SEQ ID NO 18
<211> LENGTH: 21
<212> TYPE: RNA
<213> ORGANISM: Artificial Sequence
<220> FEATURE:
<223> OTHER INFORMATION: Synthetically generated siRNA sequence

<400> SEQUENCE: 18
aaaagaaaag cagaccuacu c                                                21

<210> SEQ ID NO 19
<211> LENGTH: 23
<212> TYPE: RNA
<213> ORGANISM: Artificial Sequence
<220> FEATURE:
<223> OTHER INFORMATION: Synthetically generated siRNA sequence

<400> SEQUENCE: 19
gaguaggucu gcuuuucuuu ugg                                              23

<210> SEQ ID NO 20
<211> LENGTH: 21
<212> TYPE: RNA
<213> ORGANISM: Artificial Sequence
<220> FEATURE:
<223> OTHER INFORMATION: Synthetically generated siRNA sequence

<400> SEQUENCE: 20
caaaagaaaa gcagaccuac u                                                21

<210> SEQ ID NO 21
<211> LENGTH: 23
<212> TYPE: RNA
<213> ORGANISM: Artificial Sequence
<220> FEATURE:
<223> OTHER INFORMATION: Synthetically generated siRNA sequence

<400> SEQUENCE: 21
aguaggucug cuuuucuuuu ggu                                              23

<210> SEQ ID NO 22
<211> LENGTH: 21
<212> TYPE: RNA
<213> ORGANISM: Artificial Sequence
<220> FEATURE:
<223> OTHER INFORMATION: Synthetically generated siRNA sequence

<400> SEQUENCE: 22
ccaaaagaaa agcagaccua c                                                21

<210> SEQ ID NO 23
<211> LENGTH: 23
<212> TYPE: RNA
<213> ORGANISM: Artificial Sequence
<220> FEATURE:
<223> OTHER INFORMATION: Synthetically generated siRNA sequence

<400> SEQUENCE: 23
```

```
guaggucugc uuucuuuug guu                                              23

<210> SEQ ID NO 24
<211> LENGTH: 21
<212> TYPE: RNA
<213> ORGANISM: Artificial Sequence
<220> FEATURE:
<223> OTHER INFORMATION: Synthetically generated siRNA sequence

<400> SEQUENCE: 24
accaaaagaa aagcagaccu a                                               21

<210> SEQ ID NO 25
<211> LENGTH: 23
<212> TYPE: RNA
<213> ORGANISM: Artificial Sequence
<220> FEATURE:
<223> OTHER INFORMATION: Synthetically generated siRNA sequence

<400> SEQUENCE: 25
uaggucugcu uucuuuugg uuu                                              23

<210> SEQ ID NO 26
<211> LENGTH: 21
<212> TYPE: RNA
<213> ORGANISM: Artificial Sequence
<220> FEATURE:
<223> OTHER INFORMATION: Synthetically generated siRNA sequence

<400> SEQUENCE: 26
aaccaaaaga aaagcagacc u                                               21

<210> SEQ ID NO 27
<211> LENGTH: 23
<212> TYPE: RNA
<213> ORGANISM: Artificial Sequence
<220> FEATURE:
<223> OTHER INFORMATION: Synthetically generated siRNA sequence

<400> SEQUENCE: 27
aggucugcuu ucuuuuggu uuu                                              23

<210> SEQ ID NO 28
<211> LENGTH: 21
<212> TYPE: RNA
<213> ORGANISM: Artificial Sequence
<220> FEATURE:
<223> OTHER INFORMATION: Synthetically generated siRNA sequence

<400> SEQUENCE: 28
aaaccaaaag aaaagcagac c                                               21

<210> SEQ ID NO 29
<211> LENGTH: 23
<212> TYPE: RNA
<213> ORGANISM: Artificial Sequence
<220> FEATURE:
<223> OTHER INFORMATION: Synthetically generated siRNA sequence

<400> SEQUENCE: 29
ggucugcuuu ucuuuugguu uuu                                             23

<210> SEQ ID NO 30
<211> LENGTH: 21
<212> TYPE: RNA
<213> ORGANISM: Artificial Sequence
```

```
<220> FEATURE:
<223> OTHER INFORMATION: Synthetically generated siRNA sequence

<400> SEQUENCE: 30
aaaaccaaaa gaaaagcaga c                                              21

<210> SEQ ID NO 31
<211> LENGTH: 23
<212> TYPE: RNA
<213> ORGANISM: Artificial Sequence
<220> FEATURE:
<223> OTHER INFORMATION: Synthetically generated siRNA sequence

<400> SEQUENCE: 31
gucugcuuuu cuuuugguuu uug                                            23

<210> SEQ ID NO 32
<211> LENGTH: 21
<212> TYPE: RNA
<213> ORGANISM: Artificial Sequence
<220> FEATURE:
<223> OTHER INFORMATION: Synthetically generated siRNA sequence

<400> SEQUENCE: 32
acuuuaagca gaccuacucc a                                              21

<210> SEQ ID NO 33
<211> LENGTH: 23
<212> TYPE: RNA
<213> ORGANISM: Artificial Sequence
<220> FEATURE:
<223> OTHER INFORMATION: Synthetically generated siRNA sequence

<400> SEQUENCE: 33
uggaguaggu cugcuuaaag ucc                                            23

<210> SEQ ID NO 34
<211> LENGTH: 21
<212> TYPE: RNA
<213> ORGANISM: Artificial Sequence
<220> FEATURE:
<223> OTHER INFORMATION: Synthetically generated siRNA sequence

<400> SEQUENCE: 34
ccucgaaauc guacugagaa g                                              21

<210> SEQ ID NO 35
<211> LENGTH: 21
<212> TYPE: RNA
<213> ORGANISM: Artificial Sequence
<220> FEATURE:
<223> OTHER INFORMATION: Synthetically generated siRNA sequence

<400> SEQUENCE: 35
ucucaguacg auuucgaggu u                                              21

<210> SEQ ID NO 36
<211> LENGTH: 21
<212> TYPE: RNA
<213> ORGANISM: Artificial Sequence
<220> FEATURE:
<223> OTHER INFORMATION: Synthetically generated siRNA sequence

<400> SEQUENCE: 36
ccucgaauuc guucugagaa g                                              21
```

<210> SEQ ID NO 37
<211> LENGTH: 21
<212> TYPE: RNA
<213> ORGANISM: Artificial Sequence
<220> FEATURE:
<223> OTHER INFORMATION: Synthetically generated siRNA sequence

<400> SEQUENCE: 37
ucucagaacg aauucgaggu u                                         21

<210> SEQ ID NO 38
<211> LENGTH: 21
<212> TYPE: DNA
<213> ORGANISM: Artificial Sequence
<220> FEATURE:
<223> OTHER INFORMATION: Synthetically generated siRNA sequence

<400> SEQUENCE: 38
cguacgcgga auacuucgat t                                         21

<210> SEQ ID NO 39
<211> LENGTH: 21
<212> TYPE: DNA
<213> ORGANISM: Artificial Sequence
<220> FEATURE:
<223> OTHER INFORMATION: Synthetically generated siRNA sequence

<400> SEQUENCE: 39
ucgaaguauu ccgcguacgt t                                         21

<210> SEQ ID NO 40
<211> LENGTH: 21
<212> TYPE: RNA
<213> ORGANISM: Artificial Sequence
<220> FEATURE:
<223> OTHER INFORMATION: Synthetically generated siRNA sequence

<400> SEQUENCE: 40
gaugaggauc guuucgcaug a                                         21

<210> SEQ ID NO 41
<211> LENGTH: 23
<212> TYPE: RNA
<213> ORGANISM: Artificial Sequence
<220> FEATURE:
<223> OTHER INFORMATION: Synthetically generated siRNA sequence

<400> SEQUENCE: 41
ucaugcgaaa cgauccucau ccu                                       23

<210> SEQ ID NO 42
<211> LENGTH: 39
<212> TYPE: RNA
<213> ORGANISM: Artificial Sequence
<220> FEATURE:
<223> OTHER INFORMATION: Synthetically generated siRNA sequence

<400> SEQUENCE: 42
acaaaaacca aaagaaaagc agaccuacuc caaugaagc                      39

<210> SEQ ID NO 43
<211> LENGTH: 21
<212> TYPE: DNA
<213> ORGANISM: Artificial Sequence
<220> FEATURE:
<223> OTHER INFORMATION: Primer

<400> SEQUENCE: 43
acagaaaaaa gtggctcccc g                                                    21

<210> SEQ ID NO 44
<211> LENGTH: 21
<212> TYPE: DNA
<213> ORGANISM: Artificial Sequence
<220> FEATURE:
<223> OTHER INFORMATION: Primer

<400> SEQUENCE: 44
tattgctgtc aaaggaggcg g                                                    21

<210> SEQ ID NO 45
<211> LENGTH: 21
<212> TYPE: DNA
<213> ORGANISM: Artificial Sequence
<220> FEATURE:
<223> OTHER INFORMATION: Primer

<400> SEQUENCE: 45
acagaaaaaa gtggctcccc g                                                    21

<210> SEQ ID NO 46
<211> LENGTH: 20
<212> TYPE: DNA
<213> ORGANISM: Artificial Sequence
<220> FEATURE:
<223> OTHER INFORMATION: Primer

<400> SEQUENCE: 46
gcaaaccacc ctgggtgtta                                                      20

<210> SEQ ID NO 47
<211> LENGTH: 20
<212> TYPE: DNA
<213> ORGANISM: Artificial Sequence
<220> FEATURE:
<223> OTHER INFORMATION: Primer

<400> SEQUENCE: 47
cagaagccca cggcttatgt                                                      20

<210> SEQ ID NO 48
<211> LENGTH: 21
<212> TYPE: DNA
<213> ORGANISM: Artificial Sequence
<220> FEATURE:
<223> OTHER INFORMATION: Primer

<400> SEQUENCE: 48
tattgctgtc aaaggaggcg g                                                    21

<210> SEQ ID NO 49
<211> LENGTH: 17
<212> TYPE: DNA
<213> ORGANISM: Artificial Sequence
<220> FEATURE:
<223> OTHER INFORMATION: Primer

<400> SEQUENCE: 49
cgccagacct acacgcg                                                         17

<210> SEQ ID NO 50

<211> LENGTH: 21
<212> TYPE: DNA
<213> ORGANISM: Artificial Sequence
<220> FEATURE:
<223> OTHER INFORMATION: Primer

<400> SEQUENCE: 50
caggtagcgg ttgaagtgga a       21

<210> SEQ ID NO 51
<211> LENGTH: 16
<212> TYPE: DNA
<213> ORGANISM: Artificial Sequence
<220> FEATURE:
<223> OTHER INFORMATION: Primer

<400> SEQUENCE: 51
ccaccatccc cgcaca       16

<210> SEQ ID NO 52
<211> LENGTH: 20
<212> TYPE: DNA
<213> ORGANISM: Artificial Sequence
<220> FEATURE:
<223> OTHER INFORMATION: Primer

<400> SEQUENCE: 52
aacagggttt gccttggaaa       20

<210> SEQ ID NO 53
<211> LENGTH: 20
<212> TYPE: DNA
<213> ORGANISM: Artificial Sequence
<220> FEATURE:
<223> OTHER INFORMATION: Primer

<400> SEQUENCE: 53
tccaaggtgg taaagggtgg       20

<210> SEQ ID NO 54
<211> LENGTH: 19
<212> TYPE: DNA
<213> ORGANISM: Artificial Sequence
<220> FEATURE:
<223> OTHER INFORMATION: Primer

<400> SEQUENCE: 54
aggtcagcgt cagatcggc       19

<210> SEQ ID NO 55
<211> LENGTH: 19
<212> TYPE: DNA
<213> ORGANISM: Artificial Sequence
<220> FEATURE:
<223> OTHER INFORMATION: Primer

<400> SEQUENCE: 55
gaaggtgaag gtcggagtc       19

<210> SEQ ID NO 56
<211> LENGTH: 20
<212> TYPE: DNA
<213> ORGANISM: Artificial Sequence
<220> FEATURE:
<223> OTHER INFORMATION: Primer

<400> SEQUENCE: 56

```
gaagatggtg atgggatttc                                              20

<210> SEQ ID NO 57
<211> LENGTH: 21
<212> TYPE: DNA
<213> ORGANISM: Artificial Sequence
<220> FEATURE:
<223> OTHER INFORMATION: Primer

<400> SEQUENCE: 57
catcacattc acatgggtgg a                                            21

<210> SEQ ID NO 58
<211> LENGTH: 20
<212> TYPE: DNA
<213> ORGANISM: Artificial Sequence
<220> FEATURE:
<223> OTHER INFORMATION: Primer

<400> SEQUENCE: 58
ggttcaaccg catggaagtc                                              20
```